United States Patent
Krolik et al.

(10) Patent No.: US 9,820,769 B2
(45) Date of Patent: *Nov. 21, 2017

(54) FLOW RESTORATION SYSTEMS AND METHODS FOR USE

(71) Applicant: Hotspur Technologies, Inc., Mountain View, CA (US)

(72) Inventors: Jeffrey A. Krolik, Campbell, CA (US); Juan Domingo, Lathrop, CA (US); Daryush Mirzaee, Sunnyvale, CA (US); James H. Dreher, Santa Monica, CA (US)

(73) Assignee: Hotspur Technologies, Inc., Mountain View, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 13/655,688

(22) Filed: Oct. 19, 2012

(65) Prior Publication Data

US 2013/0289589 A1 Oct. 31, 2013
US 2017/0296215 A9 Oct. 19, 2017

Related U.S. Application Data

(62) Division of application No. 12/564,892, filed on Sep. 22, 2009, now Pat. No. 8,298,252.

(Continued)

(51) Int. Cl.
*A61B 17/221* (2006.01)
*A61B 17/3207* (2006.01)
(Continued)

(52) U.S. Cl.
CPC ........ *A61B 17/3207* (2013.01); *A61B 17/221* (2013.01); *A61B 17/320725* (2013.01);
(Continued)

(58) Field of Classification Search
CPC .......... A61B 17/221; A61B 17/320725; A61B 2017/2215; A61B 17/3207; A61B 2017/320741
(Continued)

(56) References Cited

U.S. PATENT DOCUMENTS 4,273,128 A 6/1981 Lary
4,653,496 A * 3/1987 Bundy et al. ................. 606/159
(Continued)

FOREIGN PATENT DOCUMENTS

EP 0820729 A1 1/1998
JP 2001-506912 A 5/2001
(Continued)

OTHER PUBLICATIONS

Invitation to Respond to Written Opinion dated May 7, 2012, as received in corresponding Singaporean Patent Application No. 201102023-7.
(Continued)

*Primary Examiner* — Kathleen Holwerda
(74) *Attorney, Agent, or Firm* — Baker & Hostetler LLP

(57) ABSTRACT

Apparatus and methods are provided for removing obstructive material within a body lumen. The apparatus includes a macerator device deployable from a sheath that includes an expandable cage carried by a shaft and within a constraint tube. The shaft is movable relative to the constraint tube for deploying and expanding the cage within a body lumen such that an open end of the cage is oriented towards obstructive material. The cage is advanced to capture the material or the material is directed into the cage using an expandable member expanded beyond the material and retracted to direct the material into the cage. The cage is withdrawn into the constraint tube to compress the cage radially inwardly. Materials extending through apertures in the cage are
(Continued)

sheared off by a sharpened edge of the constraint tube. The smaller, sheared off particles are then aspirated from the body lumen through the sheath.

27 Claims, 16 Drawing Sheets

Related U.S. Application Data

(60) Provisional application No. 61/099,171, filed on Sep. 22, 2008, provisional application No. 61/143,603, filed on Jan. 9, 2009, provisional application No. 61/152,227, filed on Feb. 12, 2009.

(51) Int. Cl.
*A61B 17/00* (2006.01)
*A61B 17/22* (2006.01)

(52) U.S. Cl.
CPC .......... *A61B 2017/00867* (2013.01); *A61B 2017/2215* (2013.01); *A61B 2017/22067* (2013.01); *A61B 2017/22069* (2013.01); *A61B 2017/22079* (2013.01); *A61B 2017/320741* (2013.01)

(58) Field of Classification Search
USPC .................................... 606/127, 159, 200
See application file for complete search history.

(56) References Cited

U.S. PATENT DOCUMENTS

| | | | |
|---|---|---|---|
| 4,890,611 A | 1/1990 | Monfort et al. | |
| 4,894,051 A | 1/1990 | Shiber | |
| 4,921,478 A | 5/1990 | Solano et al. | |
| 4,926,858 A * | 5/1990 | Gifford et al. | 606/159 |
| 5,192,290 A | 3/1993 | Hilal | |
| 5,372,601 A | 12/1994 | Lary | |
| 5,423,846 A | 6/1995 | Fischell | |
| 5,643,304 A | 7/1997 | Schechter et al. | |
| 5,766,191 A | 6/1998 | Trerotola | |
| 5,843,103 A | 12/1998 | Wulfman | |
| 5,868,768 A | 2/1999 | Wicherski et al. | |
| 5,954,737 A | 9/1999 | Lee | |
| 6,036,708 A * | 3/2000 | Sciver | 606/159 |
| 6,099,534 A * | 8/2000 | Bates et al. | 606/127 |
| 6,306,151 B1 | 10/2001 | Lary | |
| 6,413,235 B1 | 7/2002 | Parodi | |
| 6,454,775 B1 | 9/2002 | Demarais et al. | |
| 6,620,179 B2 | 9/2003 | Boock et al. | |
| 6,638,245 B2 | 10/2003 | Miller et al. | |
| 6,666,874 B2 | 12/2003 | Heitzmann et al. | |
| 6,945,977 B2 | 9/2005 | Demarais et al. | |
| 7,070,576 B2 | 7/2006 | O'Brien et al. | |
| 7,179,269 B2 | 2/2007 | Welch et al. | |
| 7,220,269 B1 | 5/2007 | Ansel et al. | |
| 7,250,042 B2 | 7/2007 | Kataishi et al. | |
| 7,285,126 B2 * | 10/2007 | Sepetka et al. | 606/200 |
| 7,507,246 B2 | 3/2009 | McGuckin et al. | |
| 7,517,352 B2 | 4/2009 | Evans et al. | |
| 7,833,240 B2 | 11/2010 | Okushi et al. | |
| 8,298,252 B2 * | 10/2012 | Krolik et al. | 606/159 |
| 9,198,687 B2 * | 12/2015 | Fulkerson | A61B 17/221 |
| 2002/0010487 A1 | 1/2002 | Evans et al. | |
| 2003/0130680 A1 | 7/2003 | Russell | |
| 2003/0163158 A1 | 8/2003 | White | |
| 2004/0006361 A1 | 1/2004 | Boyle et al. | |
| 2004/0260333 A1 | 12/2004 | Dubrul et al. | |
| 2006/0058837 A1 | 3/2006 | Bose et al. | |
| 2006/0074442 A1 | 4/2006 | Noriega et al. | |
| 2006/0106407 A1 | 5/2006 | McGuckin et al. | |
| 2006/0253145 A1 | 11/2006 | Lucas | |
| 2007/0208361 A1 | 9/2007 | Okushi et al. | |
| 2007/0239182 A1 | 10/2007 | Glines et al. | |
| 2008/0125798 A1 | 5/2008 | Osborne et al. | |
| 2008/0228209 A1 | 9/2008 | DeMello et al. | |
| 2008/0269798 A1 | 10/2008 | Ramzipoor et al. | |
| 2008/0312681 A1 * | 12/2008 | Ansel et al. | 606/200 |
| 2009/0076539 A1 | 3/2009 | Valaie | |

FOREIGN PATENT DOCUMENTS

| | | |
|---|---|---|
| JP | 2003-023563 | 8/2003 |
| JP | 2003-230563 A | 8/2003 |
| JP | 2003230563 A | 8/2003 |
| JP | 2004-520893 A | 7/2004 |
| JP | 2004520893 A | 7/2004 |
| WO | WO9117711 A1 | 11/1991 |
| WO | WO 99/20335 | 4/1999 |
| WO | WO9920335 A1 | 4/1999 |
| WO | WO 02/055146 | 7/2002 |
| WO | WO02055146 A1 | 7/2002 |
| WO | WO-2005/079678 A1 | 9/2005 |

OTHER PUBLICATIONS

Notice of Allowance dated Mar. 18, 2014, as received in corresponding Japanese Patent Application No. 2011-528080, and an English language translation of the same.
Notice of Rejection dated Sep. 17, 2013, as received in corresponding Japanese Patent Application No. 2011-528080, and an English language translation of the same.
Office Action dated Feb. 5, 2013, as received in corresponding Chinese Patent Application No. 200980141805.5, and an English language translation of the same.
International Preliminary Report on Patentability dated Mar. 31, 2011, as received in corresponding International Application No. PCT/US2009/057918.
International Search Report and Written Opinion dated Apr. 27, 2010, as received in corresponding International Application No. PCT/US2009/057918.
Extended European Search Report for EP 09774001.3; dated Mar. 4, 2015 (10 pages).

* cited by examiner

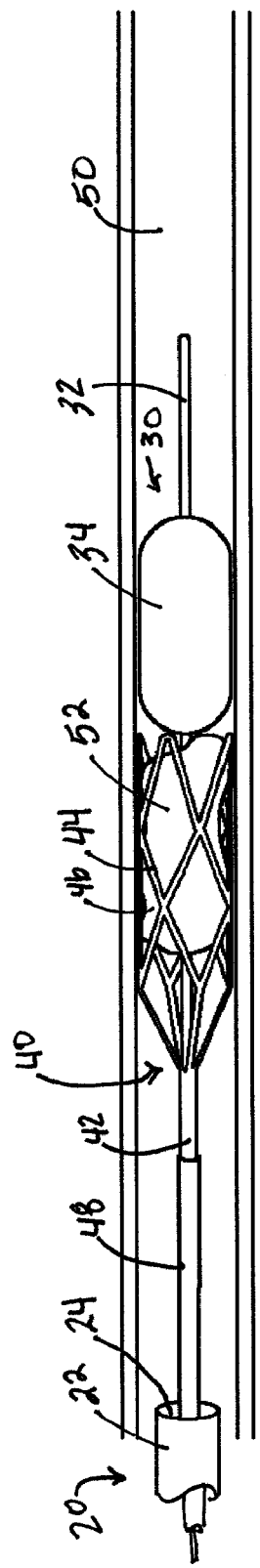
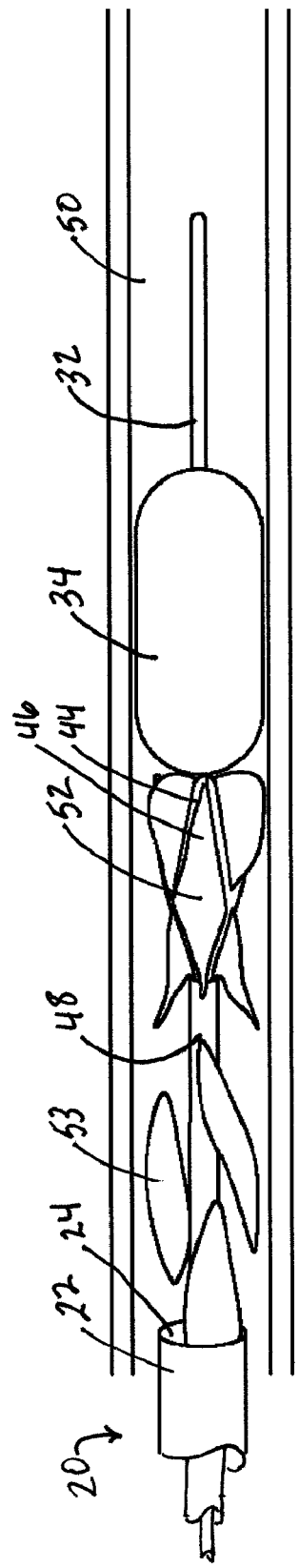
FIG. 9
FIG. 10

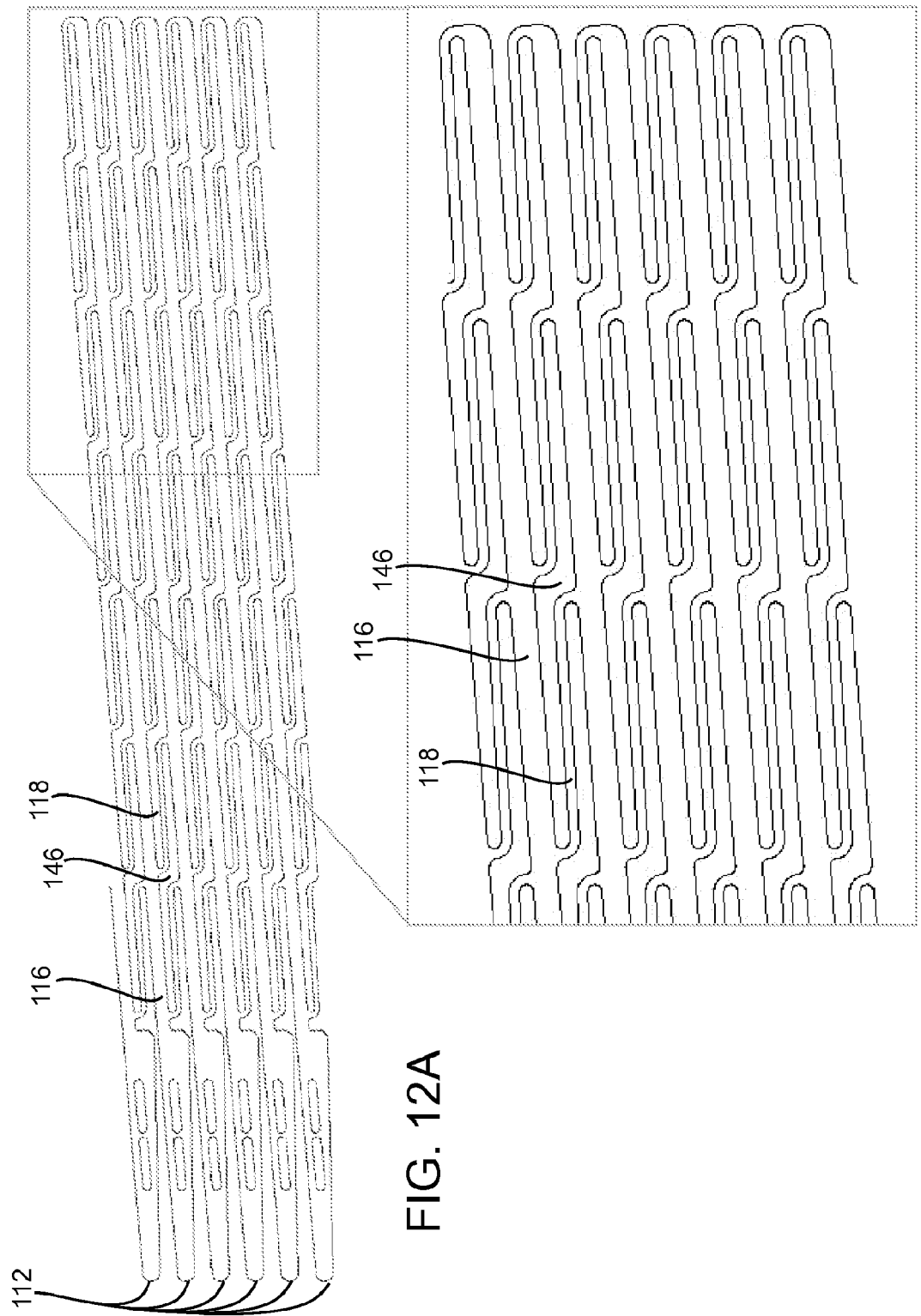

FLOW RESTORATION SYSTEMS AND METHODS FOR USE

RELATED APPLICATIONS

This application is a divisional of, and claims the benefit of U.S. patent application Ser. No. 12/564,892, filed on Sep. 22, 2009, which claims the priority of U.S. provisional application No. 61/099,171, filed on Sep. 22, 2008, provisional application No. 61/143,603, filed on Jan. 9, 2009, and provisional application No. 61/152,227, filed on Feb. 12, 2009, which are all incorporated by reference herein, as if fully set forth in their entirety.

FIELD OF THE INVENTION

The present invention relates generally to apparatus for treating obstructive material, e.g., thrombus, stenosis, and/or unwanted material within a body lumen of a patient, e.g., within a tubular graft, aorta-venous fistula, blood vessel, and the like. More particularly, the present invention relates to apparatus for removing or otherwise capturing thrombus or other obstructive material within a body lumen, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

Another approach to removing the adherent material is to advance a rotating structure that can abrade the surface of the adherent material or become entangled in the adherent material, thereby forcing the adherent material to release from the vessel wall. For example, the Arrow Treratola device has several helical wires that expand radially outward to contact the vessel wall. These wires are spun at a high speed via a driveshaft connected to an electric motor in the hand piece of the device. During operation, the Treratola device rubs against the inside wall of the vessel as it is advanced. Upon engaging adherent material, the device abrades the inside surface of that material, and in many cases, the device may break through the interface between the adherent material and the vessel wall. In this event, the adherent material can be peeled off the vessel wall and become wrapped around the helical wires of the Treratola device.

While this may address the immediate goal of removing the adherent material from the vessel wall, it is often difficult to remove the material from the vessel itself since the Treratola device does not offer any method to unwind or aspirate the material. As the Treratola device is removed from the vessel, it typically passes through a closefitting orifice such as an introducer sheath. Any material that is wound around the Treratola device is typically pushed off as it enters the sheath, and such material thus remains in the vessel.

Accordingly, apparatus and methods for removing material from aorta-venous grafts, blood vessels, or other body lumens would be useful.

SUMMARY

The present invention is directed to apparatus for treating a body lumen of a patient, e.g., a tubular graft, aortavenous fistula, blood vessel, and the like. More particularly, the present invention is directed to apparatus for removing or otherwise capturing thrombus or other obstructive material within a body lumen, and to methods for making and using such apparatus.

In accordance with one embodiment, a system is provided for removing obstructive material from a body lumen. The system includes an outer tubular member comprising a proximal end, a distal end, and a lumen extending between the proximal and distal ends. Optionally, an annular expandable occlusion member may be provided on the outer tubular member distal end. The system also includes a macerator device insertable through the lumen and comprising an elongate shaft, an expandable cage coupled to a distal end of the elongate shaft, and a constraint tube having a distal opening with a sharpened edge, wherein the shaft and the cage are axially moveable relative to the constraint tube. Optionally, the constraint tube may be fixedly coupled to an inner surface of the outer tubular member or the constraint tube may be movable independently of the outer tubular member.

The cage may include a plurality of apertures, and the distal sharpened edge of the constraint tube may be configured for shearing off material that protrudes through the apertures as the cage is proximally withdrawn into the constraint tube. Optionally, the inner surface of the cage may include a plurality of inwardly protruding barbs. The cage may include distal protruding structures and/or, thick struts and thin struts connecting the thick struts together. Optionally, one or more control wires may be coupled to the distal protruding structures of the cage, wherein the control wire(s) may be configured for drawing the protruding structures together into a closed configuration when the cage is in an expanded configuration. Optionally, a driveshaft may be operably coupled to the cage for causing the cage to rotate during advancement through the body lumen or the system may include an actuator for manually rotating the cage. In exemplary embodiments, the distal protruding structures may have a smooth edge, a slotted edge, or a serpentine edge.

In an exemplary embodiment, the system may further include an elongate treatment member comprising an expandable treatment element selectively expandable for directing the obstructive material within the body lumen into the cage when the cage is in an expanded configuration. The elongate treatment member may be insertable through a lumen in the macerator device shaft. Alternatively, the elongate treatment member may be insertable through the outer tubular member lumen adjacent to the macerator device shaft. Optionally, in this alternative, the cage may have an uninterrupted path or other opening through which the elongate treatment member may pass.

In accordance with another embodiment, a method is provided for removing obstructive material from a body lumen that includes introducing an outer tubular member into the body lumen, the outer tubular member including a lumen and a distal opening. A macerator device may be introduced through the outer tubular member lumen into the body lumen. In an exemplary embodiment, the macerator device may include an elongate shaft, an expandable cage coupled to a distal end of the elongate shaft, and a constraint tube having a distal opening. The expandable cage may be deployed out of the constraint tube distal opening by distally advancing the elongate shaft relative to the constraint tube, and expanded within the body lumen. Obstructive material may be captured within the cage, and then the cage may be proximally withdrawn into the constraint tube. Material that protrudes through apertures in the cage as the cage collapses may be sheared off, e.g., by a sharpened edge of the constraint tube distal opening. In addition or alternatively, sheared off material may be aspirated into the outer tubular member distal opening. Optionally, the method may also include expanding an occlusion element on the outer tubular member distal end, e.g., to prevent obstructive material from passing proximally beyond the distal end of the outer tubular member.

In an exemplary embodiment, the method may further include introducing an elongate treatment member including a distal expandable treatment element through the outer tubular member lumen and into the body lumen such that the expandable treatment element, in a collapsed configuration, is positioned distal to the obstructive material and the cage is positioned proximal to the obstructive material.

The expandable treatment element may be expanded and proximally withdrawn towards the expanded cage such that obstructive material is withdrawn into the cage by the expandable treatment element.

In another exemplary embodiment, the method may also include advancing the expanded cage towards the obstructive material and rotating the cage during advancement until the obstructive material becomes entangled in a distal portion of the cage. Rotation of the cage may cause obstructive material to be separated from the vessel wall, and the cage may be withdrawn into the constraint tube. The withdrawal may release the obstructive material from the cage distal portion and/or withdraw the obstructive material into the constraint tube. Optionally, the cage may be redeployed, expanded, and/or withdrawn, one or more additional times, e.g., to separate and/or withdraw obstructive material into the cage.

In accordance with another embodiment, an apparatus is provided for removing obstructive material from a body lumen that includes an outer tubular member including a proximal end, a distal end sized for introduction into a body lumen, and a lumen extending between the proximal and distal ends; an elongate shaft including proximal and distal ends and movable axially within the tubular member lumen; and an expandable macerator cage including a first end attached to the distal end of the shaft and a second free end.

The cage is expandable from a collapsed configuration when the cage is disposed within the tubular member lumen and an expanded configuration when the cage is deployed from the tubular member lumen.

In one embodiment, the cage includes a tubular structure including a wall extending between the first and second ends, the second end defining an opening communicating with an interior of the cage in the expanded configuration for capturing obstructive material within the interior of the cage. The wall may include a plurality of struts and/or apertures such that, when the cage is withdrawn back into the tubular member lumen after capturing obstructive material therein, the distal end of the tubular member slidably engages the wall of the cage or otherwise separates obstructive material captured by the cage that extends through the apertures and the cage is compressed back towards the collapsed configuration.

In accordance with still another embodiment, a system is provided for removing obstructive material from a body lumen that includes an outer tubular member including a proximal end, a distal end sized for introduction into a body lumen, and a lumen extending between the proximal and distal ends; an obstruction device deployable from the tubular member to a location beyond obstructive material intended to be removed, the obstruction device including an expandable member on a distal end thereof; and a macerator device. The macerator device may include an expandable cage carried on a distal end of a shaft and a constraint tube for maintaining the cage in a collapsed configuration, e.g., to allow the macerator device to be introduced into the body lumen through the tubular member lumen. The cage may be deployable from a distal end of the constraint tube and expandable to an expanded configuration within a body lumen. In one embodiment, the cage may include an open end communicating with an interior of the cage in the expanded configuration for capturing obstructive material within the interior of the cage.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 7-10 are cross-sectional views of a body lumen within a patient's body, showing a method for removing obstructive material within the body lumen.

FIG. 12A is a top view of a flat pattern that may be incorporated into the macerator device cage of FIGS. 11A and 11B.

FIG. 12B is a detail of a portion of the flat pattern of FIG. 12A.

DETAILED DESCRIPTION OF THE EXEMPLARY EMBODIMENTS

Figure 1:
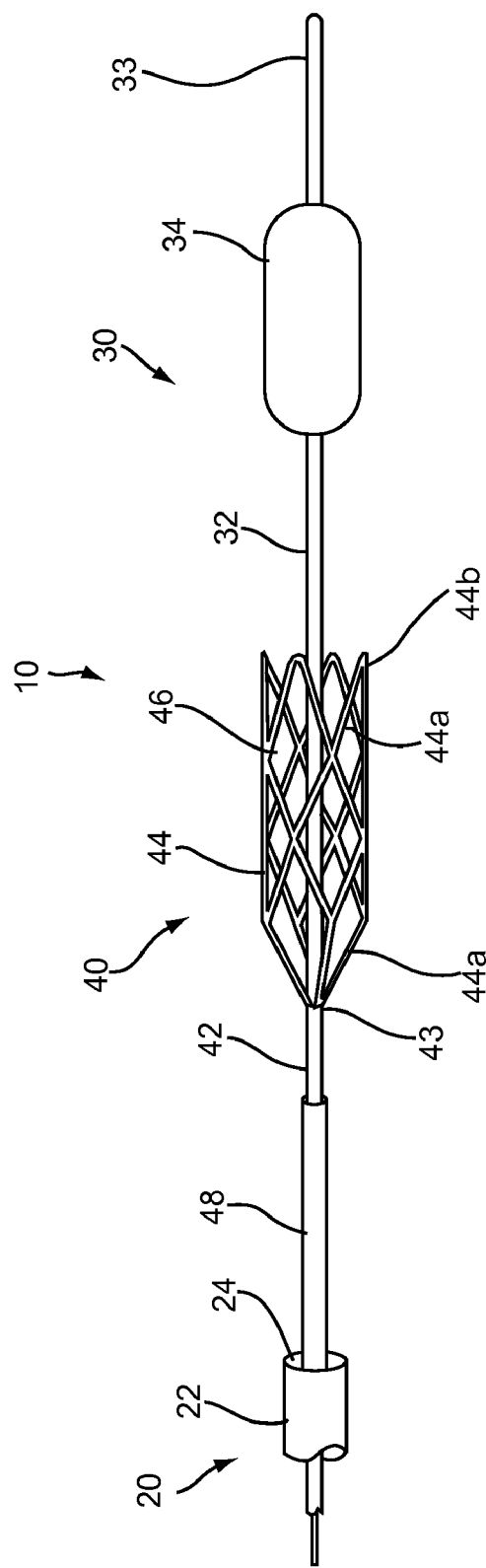
FIG. 1 is a side view of an exemplary embodiment of a flow restoration system including an occlusion device and a macerator device deployable from an access sheath.

Turning to the drawings, FIG. 1 shows an exemplary embodiment of an apparatus 10 for treating a body lumen, e.g., for removing thrombus, clots, objects, debris, and/or other unwanted or obstructive material from within the body lumen, such as a blood vessel, aorta-venous fistula, tubular graft, and the like. Generally, the apparatus 10 includes an outer access sheath or other tubular member 20, and, optionally, an obstruction device 30 and a macerator device 40, which together may provide a flow restoration system, e.g., for removing obstructive material from within body lumens in a patient's body. In addition, such a system may include one or more additional components not depicted, e.g., one or more guidewires, syringes or other sources of inflation media and/or vacuum, and the like, within the body lumen.

The sheath 20 may be an elongate tubular body, e.g., an introducer or procedure sheath, including a proximal end (not shown), a distal end 22 sized for introduction into a body lumen, and a lumen 24 extending between the proximal end and the distal end 22. The sheath 20 may be configured for percutaneous placement within a body lumen, e.g., including a rounded or otherwise substantially atraumatic tip to facilitate advancement into and/or along body lumens within a patient's body.

The sheath 20 may have a substantially uniform construction along its length, or alternatively, the construction may be varied. For example, a proximal portion of the sheath 20 may be substantially rigid or semi-rigid to facilitate advancement of the apparatus 10 by pushing or otherwise manipulating the proximal end. In addition or alternatively, a distal portion of the sheath 20 may be flexible, e.g., to facilitate bending and/or advancement through tortuous anatomy without substantial risk of kinking or buckling. In exemplary embodiments, the sheath 20 may be formed from materials such a metal, plastic, e.g., PEEK, Grilamed L25, and the like, or composite materials. The sheath 20 may have a length between about five and one hundred thirty centimeters (5-130 em) and an outer diameter between about 1.6 to 2.0 millimeters, and the lumen 24 may have a diameter between about 1.4 and 1.8 millimeters.

Optionally, the sheath 20 may include a handle or hub on the proximal end (not shown). The handle may be shaped to facilitate holding or manipulating the apparatus 10 or individual components of the apparatus 10, as described further below. In addition, the handle may include a port communicating with the lumen 24, e.g., for infusing fluid into the lumen 24 and/or aspirating material from the lumen 24, e.g., around the macerator device 40 and/or obstruction device 30. For example, a syringe, vacuum line, and the like may be coupled to the port for aspirating obstructive material received within the lumen 24 of the sheath 20 and/or disposed adjacent the distal end 22 within a body lumen, as described further below.

Figure 2A:
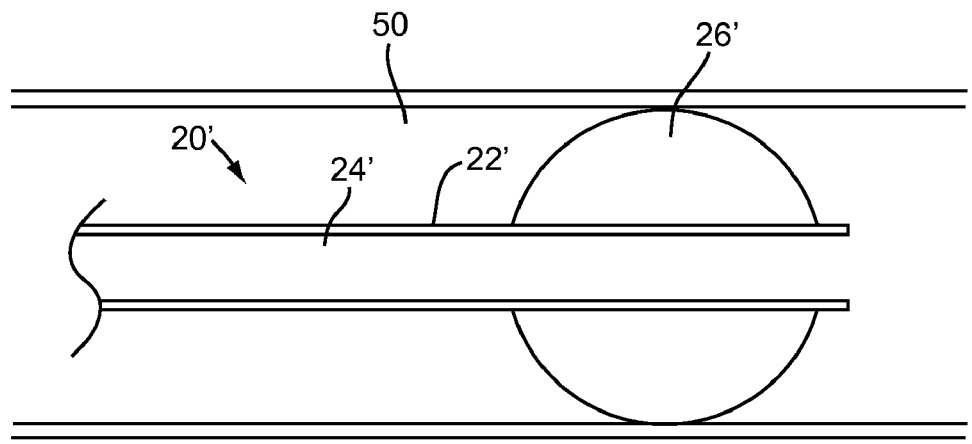
FIG. 2A is a cross-sectional side view of an access sheath that may be included in the system of FIG. 1, including an expandable member on a distal end of the access sheath.

Optionally, the sheath 20 may include an expandable member or other occlusion element carried on the distal end 22, e.g., to stabilize the sheath 20 within a body lumen and/or to seal the body lumen from fluid flow past the distal end 22 during a procedure. For example, FIG. 2A shows a sheath 20' including an expandable member 26' on its distal end 22' within a body lumen 50. The expandable member 26' may be a compliant balloon, e.g., formed from compliant material that may expand elastically proportional to the amount of inflation media delivered into the balloon 26,' a semi-compliant balloon, or a non-compliant balloon, e.g., a PTA balloon, if desired. In this embodiment, the sheath 20' may include an inflation lumen (not shown) extending from the proximal end of the sheath 20' to the distal end 22' and communicating with an interior of the balloon 26.' A source of inflation media and/or vacuum, e.g., a syringe with saline or other fluid (not shown), may be coupled to the proximal end of the sheath 20' for delivering inflation media into the balloon 26' via the inflation lumen and/or aspirating fluid from the balloon 26,' e.g., to facilitate collapsing the balloon 26' after a procedure. Alternatively, the expandable member 26' may be mechanically or otherwise expandable, e.g., including an expandable frame or other structure within or otherwise coupled to a membrane (not shown).

The expandable member 26' may be expandable from a low profile, collapsed configuration, e.g., disposed against the outer surface of the sheath 20' to facilitate introduction of the sheath 20,' and a high profile, expanded configuration, e.g., to engage or otherwise contact an inner surface of a body lumen 50 within which the sheath 20' is introduced. In the expanded configuration, the expandable member 26' may provide a substantially fluid tight seal within the body lumen 50, e.g., to prevent substantial physiologic flow along the body lumen 50, which may otherwise allow particles of loose material to move past the sheath 20 into other parts of the patient's body where they may cause harm.

In addition or alternatively, the expandable member 26' may also substantially secure and/or stabilize the sheath within the body lumen 50, e.g., to prevent inadvertent movement of the sheath 20' within the body lumen 50 during treatment.

During use, the expandable member 26' may be maintained in the low profile configuration when the sheath 20' is introduced, and then expanded to the high profile configuration once the sheath 20' is positioned within the body lumen 50 being treated. The expandable member 26' may remain expanded as obstructive material is removed from the body lumen 50 via the sheath 20' or other component of the apparatus 10, as described further below. Once the body lumen 50 is sufficiently treated, the expandable member 26' may be collapsed to restore physiologic flow within the body lumen 50.

Figure 2B:
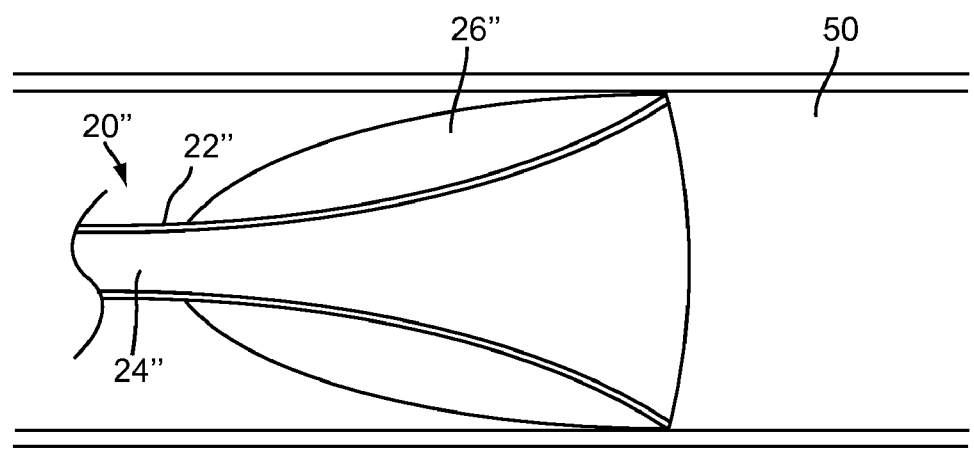
FIG. 2B is a cross-sectional side view of an alternative embodiment of an access sheath that may be included in the system of FIG. 1, including an expandable member on a distal end of the access sheath.

In an alternative embodiment shown in FIG. 2B, an access sheath 20" may be provided that includes an expandable member 26" that extends beyond the distal end 22" of the sheath 20" to provide an expandable distal tip for the sheath 20." Thus, the expandable member 26" may provide a conical or other transition extending from an enlarged distal tip towards the lumen 24" of the sheath 20," e.g., such that maceration of obstructive material may be performed within or adjacent the distal tip of the expandable member 26" if desired. During maceration, particles of obstructive material may be liberated within or adjacent the lumen 24" of the sheath 20," thereby facilitating aspiration of the particles from the body lumen 50 into the lumen 24." Additional information on the access sheath 20" and/or expandable member 26" may be found in PCT/US09/53237, filed Aug. 8, 2009, the entire disclosure of which is expressly incorporated by reference herein.

Referring back to FIG. 1, the obstruction device 30 generally includes a shaft or other elongate member 32 including a proximal end (not shown), a distal end 33 sized for introduction through the sheath 20, e.g., via the lumen 24, and carrying an expandable obstruction or treatment member 34 on the distal end 33. Generally, the obstruction member 34 is expandable from a collapsed configuration (not shown), e.g., sized for introduction through the lumen 24 of the sheath 20, and an expanded configuration (shown in FIG. 1) for engaging or otherwise contacting a wall of a body lumen within which the obstruction member 34 is expanded. In an exemplary embodiment, the obstruction member 34 may be a balloon, e.g., a compliant, semi-compliant, or non-compliant balloon, expandable to a substantially spherical or cylindrical shape. In this embodiment, the shaft 32 may include an inflation lumen (not shown) in communication with an interior of the obstruction member 34, e.g., for selectively expanding and collapsing the obstruction member 34. Optionally, the obstruction member 34 may include a core wire and/or helical structure (not shown), e.g., such that the obstruction member may adopt a helical shape in the expanded configuration.

Exemplary devices that may be used for the obstructive device 30 are disclosed in co-pending application Ser. No. 12/497,135, filed Jul. 2, 2009, the entire disclosure of which is expressly incorporated by reference herein. Alternatively, the obstruction member 34 may include a frame or other mechanically expandable structure (not shown), if desired.

With continued reference to FIG. 1, the macerator device 40 generally includes a shaft or other elongate member 42 including a proximal end (not shown), a distal end 43 also sized to fit within the lumen 24 of the sheath 20, and an expandable cage 44 carried on the distal end 43. Optionally, the shaft 42 may include a lumen or other track (not shown) for slidably receiving the obstruction device 30 therethrough, as described further below. In addition or alternatively, the shaft 42 may include one or more additional lumens (not shown), e.g., for receiving a guidewire or other rail (also not shown), one or more actuator wires or cables (also not shown), and the like, as described further below.

As shown, the cage 44 is an open or porous expandable structure including a closed proximal or first end 44a coupled to the shaft 42 and an open distal or second end 44b, e.g., to accommodate receiving obstructive material within the cage 44, as described further below. Generally, the cage 44 includes a plurality of struts 44a extending between the first and second ends 44a, 44b and/or around a periphery of the cage 44, thereby defining a cylindrical or other tubular outer wall including a plurality of apertures 46, e.g., at least adjacent the first end 44a. The struts 44a and/or apertures 46 may be sized to accommodate expansion and/or collapse of the cage 44 and/or to define a desired pore size that prevents particles larger than the desired pore size from escaping once captured within the cage 44, as described further below.

The cage 44 is expandable from a low-profile, collapsed configuration (not shown), e.g., to accommodate introduction through the sheath 20, and a high-profile, expanded configuration (shown in FIG. 1) where the cage 44 expands radially outwardly, e.g., to contact the wall of a body lumen within which the cage 44 is deployed and/or expanded.

Figure 3:
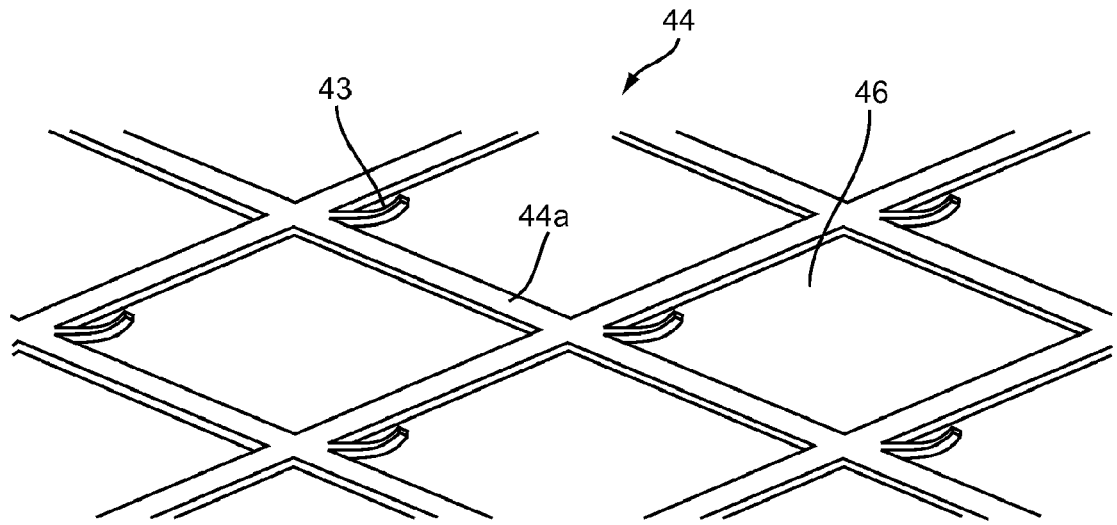
FIG. 3 is a detail of an inner surface of a cage of a macerator device that may be included in the system of FIG. 1.

Optionally, as shown in FIG. 3, the cage 44 may include a plurality of barbs or other features 41 projecting radially inwardly from the struts 44a, e.g., to engage and/or provide additional traction with obstructive material captured within the cage 44, as discussed further below.

The cage 44 may be formed from a variety of materials, e.g., capable of elastically or plastically moving between the collapsed and expanded configurations one or more times. For example, the cage 44 may be formed from elastic or superelastic materials, e.g., metals, such as stainless steel, Nitinol, and the like, plastics, or composite materials. In an exemplary embodiment, the cage 44 may be formed from a tube with portions of the tube removed to define the struts 44a and/or apertures 46, e.g., by laser cutting, etching, mechanical cutting, and the like. Alternatively, the cage 44 may be formed from a sheet also with portions removed to define the struts 44a and/or apertures 46, e.g., by laser cutting, etching, mechanical cutting, stamping, and the like, which may be rolled into a tubular shape with edges of the sheet attached together, e.g., by welding, soldering, bonding with adhesive, fusing, and the like.

The cage 44 may then be attached to the shaft 42, e.g., by substantially permanently attaching the closed end 44a around the distal end 43 of the shaft 42, e.g., by crimping, bonding with adhesive, fusing, wrapping a collar, wire or other material around the closed end 44a, and the like. Thus, the closed end 43 may be fixed in the collapsed configuration, while the rest of the cage 44 may be free to expand from the collapsed configuration to the expanded configuration. In an exemplary embodiment, the cage 44 may be formed from superelastic material that may be heat treated to program the expanded configuration into the cage 44, while allowing the cage 44 to be resiliently compressed and maintained in the collapsed configuration.

Thus, in the embodiment shown in FIG. 1, the cage 44 may be a self-expanding structure, e.g., resiliently compressible radially inwardly to the collapsed configuration yet biased to expand towards the expanded configuration. Alternatively, the cage 44 may be mechanically expanded and collapsed, e.g., using an actuator (not shown) on the proximal end of the macerator device 40 coupled to the cage 44.

To maintain a self-expanding cage 44 in the collapsed configuration, e.g., during introduction through or before deployment from the sheath 20, the macerator device 40 may include a constraint tube 48 slidably disposed around the shaft 42. The constraint tube 48 may be an elongate tubular body including a proximal end (not shown), a distal end 48a, and a lumen 49 extending therebetween that is sized to receive the shaft 42 and cage 44 with the cage 44 in the collapsed configuration. Alternatively, other removable constraints may be provided around the cage 44 to maintain the cage 44 in the collapsed configuration until it is desired to deploy and expand the cage 44 within a body lumen, e.g., one or more removable wires wound around the cage 44, a tearaway sleeve, and the like (not shown).

The distal end 48a of the constraint tube 48 may be sized to be slidably disposed within the sheath 20, e.g., to accommodate introduction of the macerator device 40 through the lumen 24 of the sheath 20. The constraint tube 48 and the shaft 42 and cage 44 may be movable axially relative to one another, e.g., to allow the cage 44 to be retracted within the constraint tube 48 and/or deployed from the constraint tube 48. Thus, the constraint tube 48 may maintain the cage 44 in the collapsed configuration, e.g., during introduction into a body lumen through the sheath 20, and allow the cage 44 to be deployed from the constraint tube 48 such that the cage 44 assumes the expanded configuration.

The proximal ends (not shown) of the shaft 42 and/or constraint tube 48 may extend or otherwise be coupled to the proximal end of the sheath 20 and may be actuatable from the proximal end of the sheath 20. For example, the sheath 20 may include a handle or hub (not shown) on its proximal end, which may include one or more actuators for advancing the macerator device 40 from the distal end 22 of the sheath 20 and/or for deploying the cage 44 from and covering the cage 44 with the constraint tube 48. The shaft 42 and/or constraint tube 48 may extend into the handle, or one or more cables, wires, rods, or other actuator elements (not shown) may be coupled between the shaft 42 and/or constraint tube 48 and one or more actuators on the handle.

For example, a first actuator, e.g., a slider, button, dial, and the like, may be provided on the handle (not shown) to advance and/or retract the entire macerator device 40 relative to the sheath 20, e.g., to deploy the cage 44 from the distal end 22 of the sheath 20 while still covered by the constraint tube 48. A second actuator, e.g., another slider, button, dial, and the like (also not shown), may then be activated to expose the cage 44, e.g., by advancing the shaft 42 and cage 44 relative to the constraint tube 48 or retracting the constraint tube 48 without substantial movement of the cage 44. Exemplary handles and/or actuators that may be provided on the apparatus 10 are disclosed in application Ser. No. 12/497,135 incorporated by reference above.

Alternatively, the sheath 20 and macerator device 40 may be structurally separate devices, and the macerator device 40 may be introduced into the sheath 20, e.g., via a port or other opening in the proximal end of the sheath 20. For example, a handle or hub (not shown) may be provided on the proximal end of the sheath 20 that includes a port (also not shown) communicating with the lumen 24 that may accommodate introduction of the macerator device 40 and/or other devices therein. Optionally, the port may include one or more seals, e.g., a hemostatic seal that may accommodate receiving the macerator device 40 therein while providing a substantially fluid-tight seal to prevent bodily fluids from escaping from the lumen 24. In this alternative, the macerator device 40 itself may include a handle or hub (not shown) on its proximal end that includes one or more actuators (also not shown) for manipulating the shaft 42 and cage relative to the constraint tube 48, similar to the actuators described above.

Optionally, in a similar manner, the obstruction device 30 may be coupled to the sheath 20 and/or macerator device 40, e.g., with one or more actuators (not shown) on a handle of the apparatus 10 for deploying and/or withdrawing the obstruction device 30. Alternatively, the obstruction device 30 may be a separate device from the sheath 20 and/or macerator device 40, and the macerator device 40 may include a port for receiving the obstruction device 20, e.g., similar to the port described above.

Figure 4A:
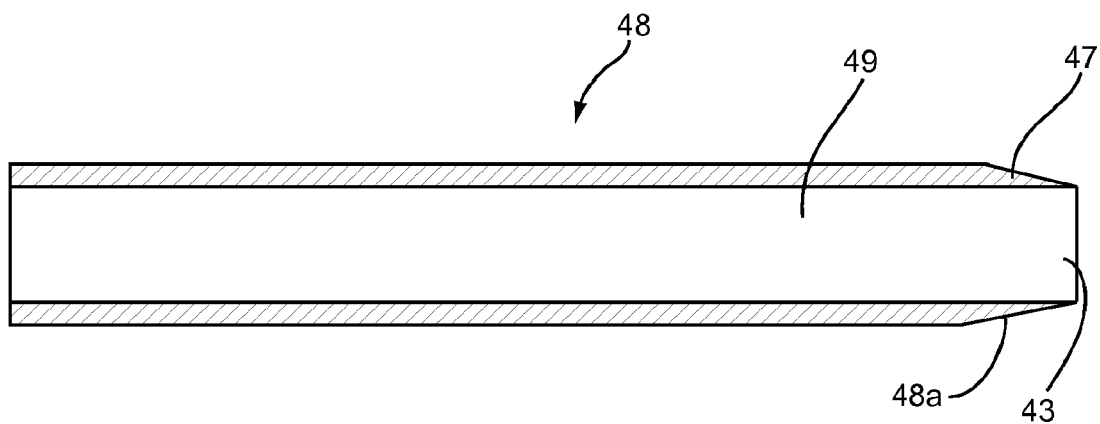
FIGS. 4A and 4B are cross-sectional side views of exemplary embodiments of a constraint tube that may be included in a macerator device in the system of FIG. 1.
Figure 4B:
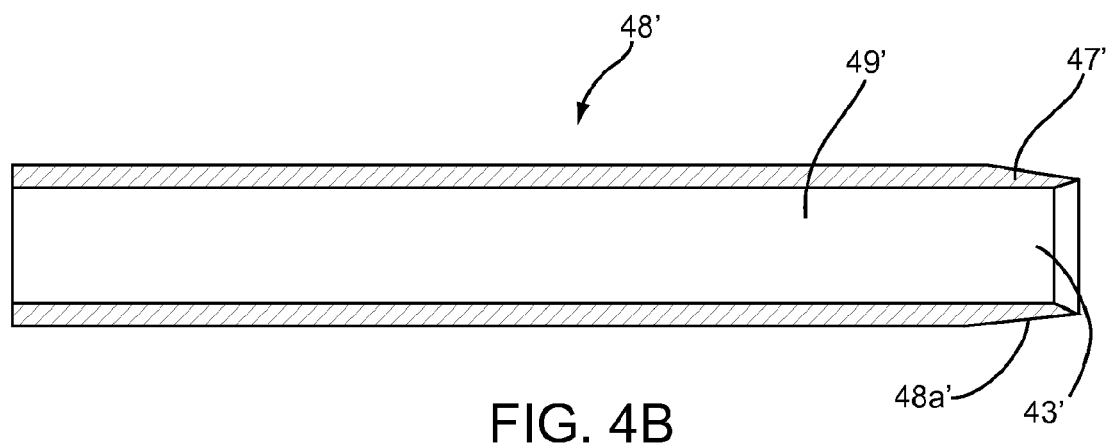

Optionally, as shown in FIGS. 4A and 4B, the constraint tube 48 may be configured to facilitate removing excess material captured by the cage 44. For example, the distal end 48a of the constraint tube 48 may include one or more features that slide or otherwise interact with the cage struts 44a, e.g., to trim excess material that extends out of the cage apertures 46 when the cage 44 is withdrawn back into the constraint tube 48 after capturing obstructive material within the cage 44. Thus, as the cage 44 enters the constraint tube 48 and is compressed towards the collapsed configuration, the features on the distal end 48a of the constraint tube 48 may shear or otherwise trim excess material that protrudes out of the cage apertures 46.

In an exemplary embodiment, shown in FIG. 4A, the distal end 48a of the constraint tube 48 may include a sharpened edge 47 extending around a distal opening 43 communicating with the lumen 49 that is suitable for cutting off excess obstructive material that may protrude through the apertures 46 of the cage 44. In the embodiment shown in FIG. 4A, the sharpened edge 47 may be a single-ground edge, e.g., that may shear along the outer surface of the cage 44 during withdrawal to cut or otherwise separate obstructive material extending through the apertures 46. Alternatively, as shown in FIG. 4B, a constraint tube 48' may be provided that includes a double-ground sharpened edge 47' extending around distal opening 43.' The double-ground sharpened edge 47' may cut excess obstructive material similarly to the single-ground edge 47, but may be more resistant to damage as the cage 44 passes into the lumen 49' of the constraint tube 48.' For example, since the cutting edge 47' has a slightly larger diameter than the lumen 49' of the constraint tube 48' itself, the cutting edge 47' may not contact the outer surface of the cage 44 during withdrawal of the cage 44 but remain spaced slightly apart from the cage 44.

Figure 5:
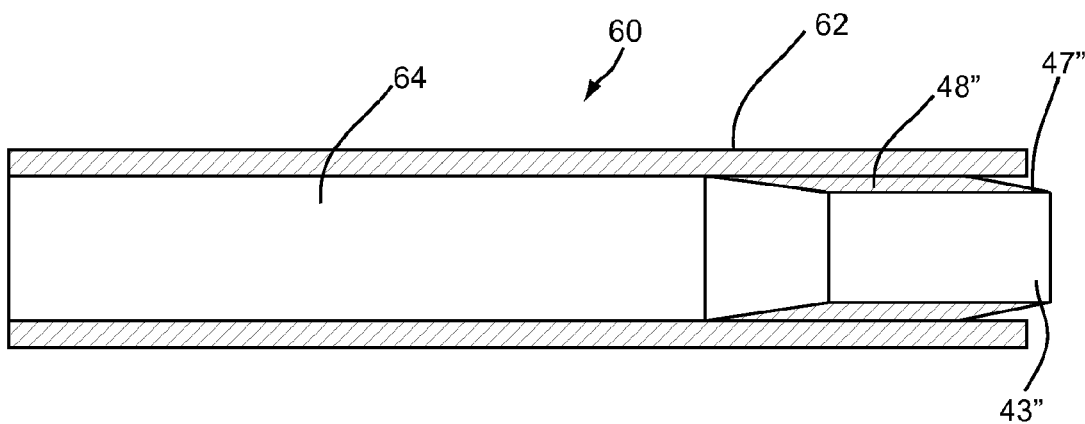
FIG. 5 is a cross-sectional side view of an alternative embodiment of an access including an integral constraint tube that may be included in the system of FIG. 1.

In an alternative embodiment, shown in FIG. 5, the constraint tube 48 shown in FIGS. 4A and 4B may be omitted, and a sheath 60 may be used to constrain the cage 44 (not shown) in the collapsed configuration during introduction and/or to remove excess material during withdrawal of the cage 44. Similar to the previous embodiments, the sheath 60 includes a proximal end (not shown), a distal end 62, and a lumen 64 extending therebetween. Unlike the previous embodiments, the sheath 60 includes a constraint tube 48" incorporated into the distal end 64, e.g., within the lumen 64.

The constraint tube 48" may be a relatively short tubular body extending a short distance into the lumen 64 and including an exposed and sharpened edge 47" around a distal opening 43," e.g., a single-ground or double-ground edge, similar to the previous embodiments. The constraint tube 48" may be substantially permanently attached within the lumen 64 or otherwise to the distal end 62, e.g., by bonding with adhesive, interference fit, fusing, sonic welding, and the like, thereby providing a transition from the distal opening 43" into the lumen 64.

During use, the cage 44 may be advanced from the lumen 64 and out of the distal opening 43" whereupon the cage 44 may freely expand towards the expanded configuration.

After unwanted material is captured within the cage 44 (as described further elsewhere herein), the cage 44 may be withdrawn back into the sheath 60 through the distal opening 43," whereupon excess obstructive material extending through the apertures 46 of the cage 44 may be cut or otherwise separated by the sharpened edge 47" as the cage 44 collapses.

In a further alternative, the sheath 20 shown in FIG. 1, may be used to constrain the cage 44 during introduction and/or withdrawal and the constraint tube 48 may be omitted entirely. Unlike previous embodiments, however, when the cage 44 is withdrawn into the sheath 20, the cage 44 may not be collapsed to as small a size due to the relatively larger diameter of the sheath 20 compared to a constraint tube 48 introduced through the sheath 20. In this alternative, a portion of the obstructive material may remain within the cage 44 after withdrawal into the sheath 20. In other words, the macerator device cage 44 may be used to capture and remove the obstructive material without trimming off excessive obstructive material. Alternatively, the sheath 20 itself may include a sharpened distal edge (not shown) or a sharpened tip may be attached to the distal end 22 of the sheath 20 (also not shown), e.g., to cut off excess obstructive material during withdrawal of the cage 44, while obstructive material within the cage 44 is withdrawn into the sheath 20 within the cage 44.

Figure 6:
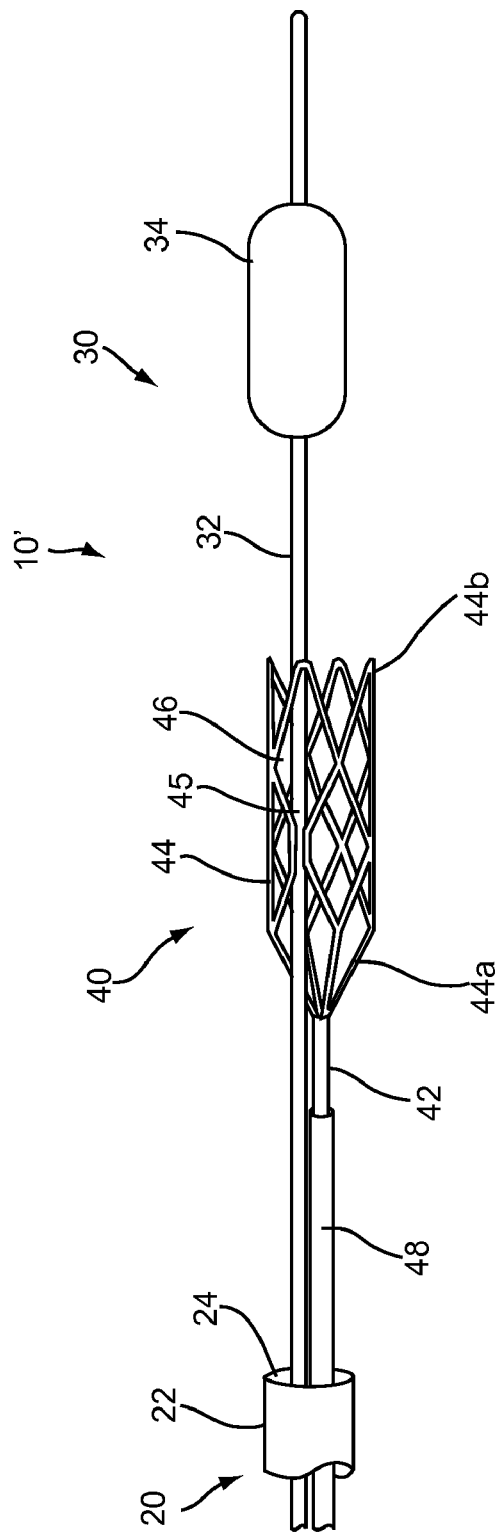
FIG. 6 is a side view of another exemplary embodiment of a flow restoration system including an occlusion device and a macerator device deployable from an access sheath.

With further reference to FIG. 1, in the embodiment shown, the shaft 42 of the macerator device 40 includes a lumen that slidably receives the shaft 32 of the obstruction device 30, e.g., such that the macerator device 40 and the obstruction device 30 have a concentric, telescoping arrangement relative to one another. Alternatively, as shown in FIG. 6, an apparatus 10' may be provided in which a macerator device 40 and an obstruction device 30 are provided in a side-by-side arrangement relative to an outer sheath 20. In this alternative, the sheath 20, obstruction device 30, and macerator device 40 may be constructed similar to the embodiments described above. Optionally, the macerator device 40 may include a cage 44 that includes an uninterrupted path 45 defined by struts 44a of the cage 44 that extends axially along at least a portion of the cage 44 to accommodate the obstruction device 30 passing through the cage 44 while allowing the cage 44 to close substantially completely to the collapsed configuration.

In this embodiment, the obstruction device 30 and macerator device 40 may be received in a common lumen 24 of the sheath 20, as shown in FIG. 6. Alternatively, the sheath 20 may include separate lumens (not shown) disposed adjacent one another, each for receiving one of the obstruction device 30 and the macerator device 40. Otherwise structure and operation of the apparatus 10' may be similar to that described with reference to apparatus 10 of FIG. 1.

Turning to FIGS. 7-10, an exemplary method is shown for removing material, e.g., thrombus or other obstructive material 52, within a body lumen 50. The body lumen 50 may be a blood vessel, aorta-venous fistula, tubular graft, xenograft, and the like, e.g., within a patient's arm that communicates between an adjacent vein and artery. Alternatively, the apparatus and methods described herein may be used to treat other locations within a patient's body, e.g., within the patient's vasculature or other body lumens. Although apparatus 10 shown in FIG. 1 is shown and described in association with FIGS. 7-10, it will be appreciated that the methods described herein may be performed using any of the apparatus and systems described herein.

Figure 7:
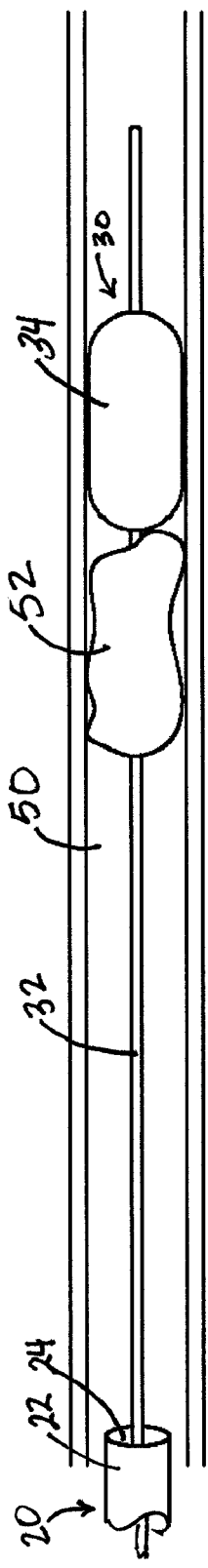

Generally, the method may involve trapping thrombus or other obstructive material between an expanded obstruction member 34 and an expanded cage 44, e.g., such that the material may be captured by the cage 44, broken into smaller particles, removed within the cage 44, and/or aspirated from the body lumen 50 through sheath 20. Initially, as shown in FIG. 7, the sheath 20 may be introduced into a body lumen 50, e.g., percutaneously from an entry site using conventional methods, and manipulated to position the distal end 22 of the sheath 20 within the body lumen 50 adjacent to and spaced apart from obstructive material 52. Optionally, if the sheath 20 includes an expandable member, e.g., balloon 26, 26' as shown in FIG. 2A or 2B, on the distal end 22, the expandable member (not shown) may be expanded any time after the distal end 22 is placed at a desired position within the body lumen 50, e.g., to prevent subsequent movement of the sheath 20 and/or to substantially seal the body lumen 50 from fluid flow proximally past the sheath 20.

In addition or alternatively, aspiration may be applied to the lumen 24 of the sheath 20, e.g., at any time after introducing the distal end 22 of the sheath 20 into the body lumen 50. For example, a syringe or vacuum line may be coupled to the proximal end of the sheath 20 and activated to apply a substantially continuous vacuum to the lumen 24 to draw loose material within the body lumen 50 into the lumen 24.

The obstruction device 30 may then be introduced into the body lumen 50 from the sheath 20 and advanced past the material 52 with the obstruction member 34 in the lowprofile configuration (not shown). For example, the obstruction device 30 may be loaded into the lumen 24 of the sheath 20 and advanced through the length of the sheath 20 into the body lumen 50, or the obstruction device 30 may be integral with or preloaded into the sheath 20 before the procedure and merely deployed from the sheath 20. Optionally, a distal tip of the obstruction device 30 may be sufficiently small and/or sharp to pass freely through the material 52 and/or may be rounded or otherwise substantially atraumatic to pass along the wall of the body lumen 50 past the material 52. Once the obstruction member 34 is positioned distally beyond the material 52, the obstruction member 34 is expanded to the high-profile condition, as shown in FIG. 7.

Figure 8:
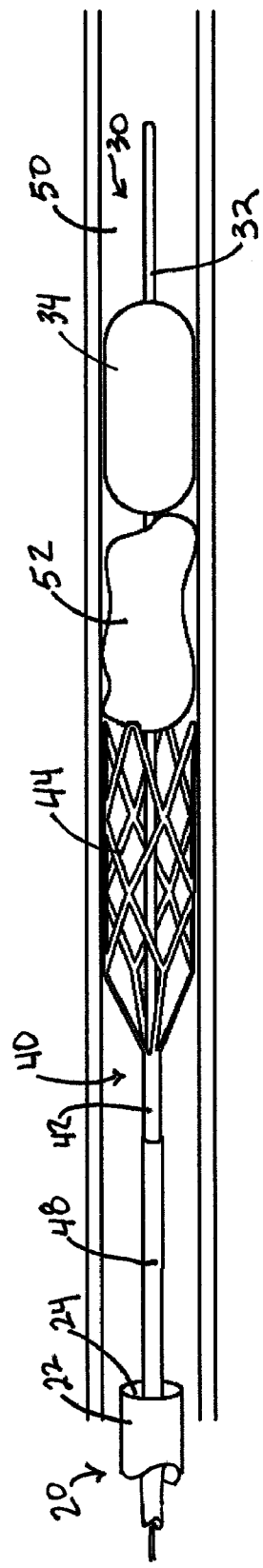

Next, with reference to FIG. 8, the macerator device 40 may be deployed from the sheath 20, e.g., over or adjacent the shaft 32 of the obstruction device 30. The macerator device 40 may be advanced until the cage 44 (maintained in the collapsed configuration within the constraint tube 48) is disposed proximal or adjacent to the material 52 opposite the expanded obstruction member 34. Thus, the obstructive material 52 may be bounded by the obstruction member 34 on one side and the macerator device 40 on the other. Once positioned within the body lumen 50, the cage 44 may be expanded within the body lumen 50, e.g., by deploying the cage from the constraint tube 48, whereupon the cage 44 may resiliently expand radially outwardly to contact the wall of the body lumen, as shown in FIG. 8.

Turning to FIG. 9, the obstruction device 30 may then be retracted proximally towards the cage 44 to pull material 52 within the body lumen 50 towards and into the macerator device cage 44, as shown. Alternatively, the cage 44 may be advanced towards the obstruction device 30 to capture material 52 within the cage 44, with the obstruction member 34 preventing distal migration of the material 52 away from the cage 44. As described above, if the cage 44 includes barbs 41, e.g., as shown in FIG. 3, the barbs 41 may partially penetrate or otherwise engage with the material 52 captured within the cage 44, e.g., to prevent migration of the material 52 relative to the cage 44.

Optionally, the obstruction device 30 and/or macerator device 40 may include a locking mechanism, e.g., one or more cooperating detents, tabs, or other features (not shown), that may substantially secure the obstruction device 30 relative to the cage 44 when the obstruction device 30 has been placed a predetermined distance from the cage 44, e.g., substantially adjacent the cage 44 such that the obstruction device 30 substantially encloses the material 52 within the cage 44, as shown in FIG. 9. Alternatively, a locking mechanism may be provided on a proximal end of the apparatus 10, e.g., on a handle (not shown), which may be locked and unlocked to selectively secure the obstruction device 30 relative to the cage 44. With the locking mechanism engaged, the obstruction device 30 may not be directed distally away from the cage 44, e.g., such that subsequent movement of the obstruction device 30 is coupled to movement of the cage 44.

Turning to FIG. 10, the macerator device cage 44 and expanded obstruction member 34 may then be directed proximally towards the sheath 20, e.g., until the cage 44 enters the constraint tube 48. If a vacuum has not been applied previously, a source of vacuum may be activated to aspirate material released within the body lumen 50 into the lumen 24 of the sheath 24, as shown. As the cage 44 is drawn into the constraint tube 48, the cage 44 may be compressed radially inwardly, thereby forcing portions of the material 52 through the apertures 46 in the cage 44. The portions of the material 52 exposed through the apertures 46 may be sheared off, e.g., by the sharpened distal edge 47, 47' (not shown, see FIGS. 4A and 4B) of the constraint tube 48, reducing the material 52 into many smaller particles 53 within the body lumen 50. The loose particles 53 may be removed from the body lumen 50, e.g., by aspiration, through the sheath lumen 24, as shown.

Notably, the reduced particle size may be a function of the size of the apertures 46 in the cage 44. Thus, the size of the cage apertures 46 may be chosen to reduce the particle size of the material 52 to a desired maximum cross-section, e.g., such that the reduced diameter particles 53 may be reliably removed though the sheath 20 without substantial risk of occluding the sheath lumen 24.

In one embodiment, the cage 44 may be compressed to a collapsed configuration as the cage 44 is withdrawn into the constraint tube 48 in which the interior space of the cage 44 is minimized, thereby squeezing substantially all of the captured material 52 through the apertures 46 of the cage 44.

The extruded and/or sheared particles 53 may then be aspirated into the lumen 24 of the sheath 20. Alternatively, the cage 44 may have sufficient interior space in the collapsed configuration such that at least some captured material may remain within the cage 44 when the cage 44 is withdrawn fully into the constraint tube 48.

With the cage 44 withdrawn fully into the constraint tube 48, the macerator device 40 and obstruction device 30 may be withdrawn into the sheath 20 and the apparatus 10 removed from the patient's body. Alternatively, the obstruction member 34 may be collapsed and the obstruction device 30 advanced through another section of obstructive material (not shown) within the body lumen 50. In this alternative, the macerator device 40 may then be redeployed to capture and remove the material, e.g., by repeating the steps described above. Optionally, the entire apparatus 10 may be introduced into another body lumen (not shown), and the obstruction device 30 and macerator device 40 redeployed to capture and/or remove obstructive material in other regions of the patient's body, if desired.

Once sufficient material has been removed, the obstruction member 34 of the obstruction device 30 may be collapsed and the obstruction device 30 may be withdrawn into the macerator device 40 or into the sheath 20 if the macerator device 40 has already been withdrawn into the sheath 20. The aspiration within the sheath 20 may be discontinued, the expandable member on the sheath 20 may be collapsed (if provided on the sheath 20), and the sheath 20 may be withdrawn from the body lumen 50.

Turning to FIGS. 11A-13, another embodiment of a macerator cage 144 is shown that may be included in any of the apparatus and/or systems described herein. Generally, the macerator cage 144 includes a closed proximal or first end 144a and an open distal or second end 144b, similar to the previous cage 44. The cage 144 may include a plurality of struts 116, 118 extending between the first and second ends 144a, 144b and/or around a periphery of the cage 144, thereby defining a cylindrical or other tubular outer wall including a plurality of apertures 146, similar to the previous cage 44.

Figure 11A:
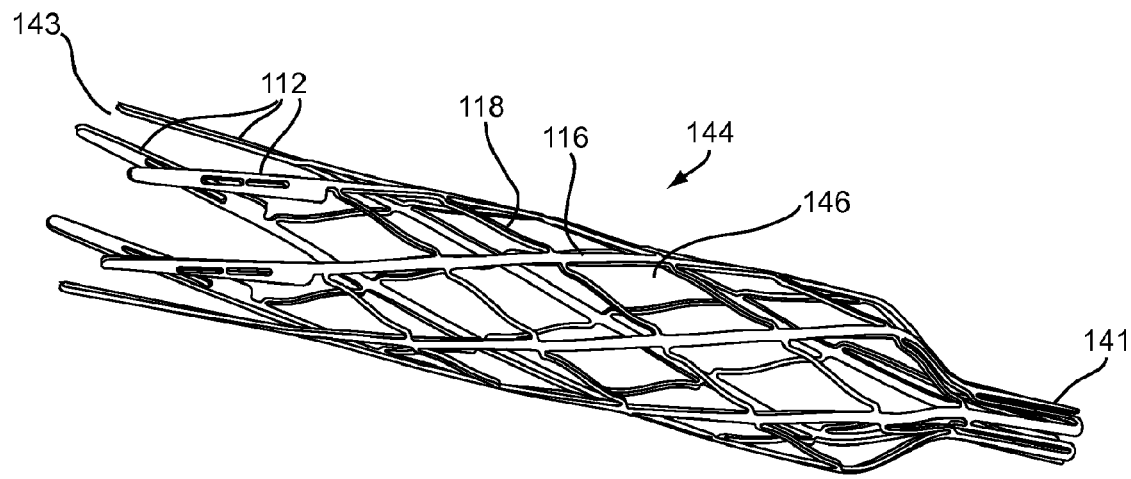
FIGS. 11A and 11B are perspective views of another exemplary embodiment of a macerator device cage in expanded and collapsed configurations, respectively.
Figure 11B:
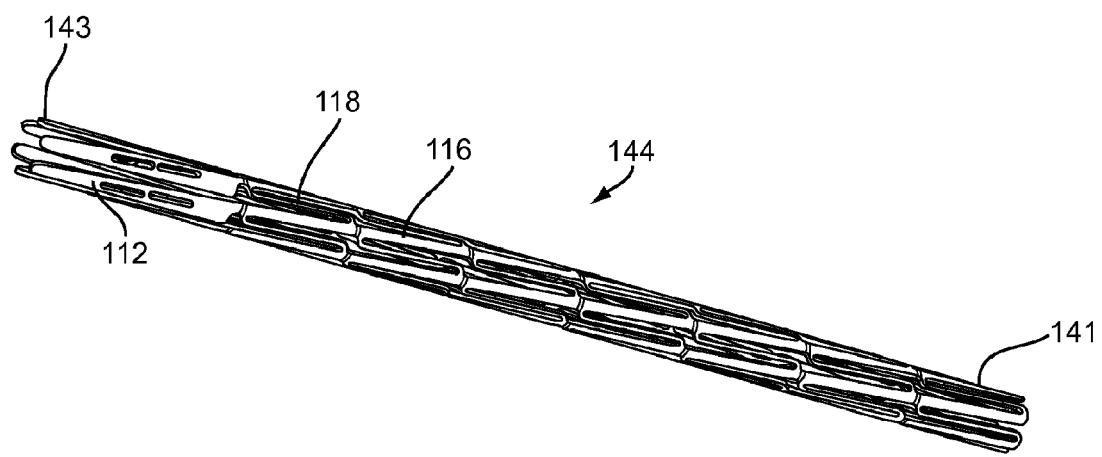

The closed end 144a of the cage 144 may include a collar portion 141, which may be attached to a macerator device shaft 42 (not shown, see, e.g., FIG. 1), while the open distal end 143 of the cage 144 may include a plurality of distally protruding elements or distal tips 112. For example, FIG. 11A shows the cage 144 in an expanded configuration in which the collar portion 141 remains compressed, e.g., due to its attachment to a shaft (not shown), and the cage 144 defines a substantially continuous diameter extending from the closed end 144a to the open end 144b. FIG. 11B shows the cage 144 in a compressed configuration, e.g., in which the cage 144 may be constrained or otherwise compressed around the shaft and/or within a constraint tube (also not shown).

Unlike the cage 44 of FIG. 1, as can be best seen in FIGS. 12A and 12B, the cage 144 includes at least two different types of struts 116, 118. For example, the cage 144 may include a plurality of relatively thick struts 116 that extend substantially continuously along a length of the cage 144, e.g., in a first helical configuration between the first and second ends 144a, 144b. In addition, the cage 144 may include a plurality of relatively thin struts 118, which may connect adjacent thick struts 116 together. As shown, the thin struts 118 are not substantially continuous as are the thick struts 116, but may extend in a discontinuous pattern helically and/or circumferentially around the cage 44. Optionally, the thin struts 118 may also have bends or other features, e.g., relatively thinned or perforated portions, that allow the struts 118 to bend relatively easily compared to the thick struts 116.

The apertures 146 may be defined by the spaces between the thick struts 116 and the thin struts 118, thereby defining a desired pore size for the cage 144. The cage 144 may be formed using similar materials and methods as those previously described above.

Figure 15A:
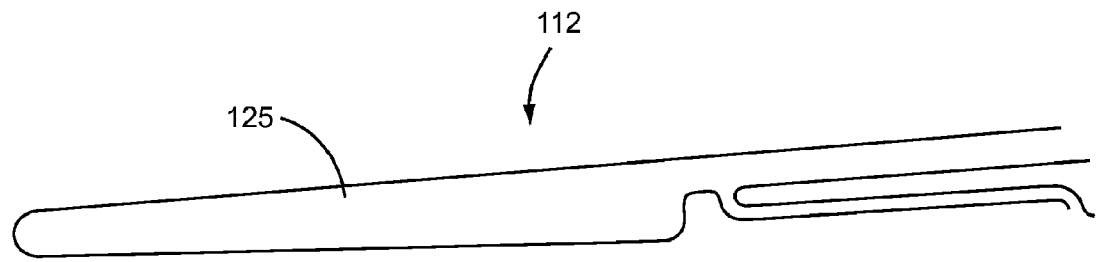
FIGS. 15A-15C are side views of alternative embodiments of distal tips that may be provided on a macerator device cage, such as the cage shown in FIGS. 11A and 11B.
Figure 15B:
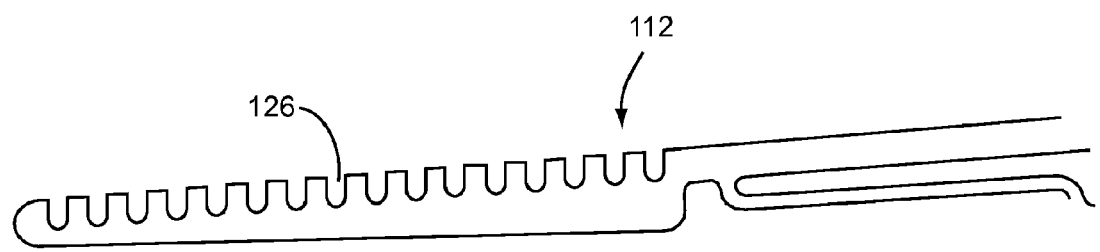
Figure 15C:
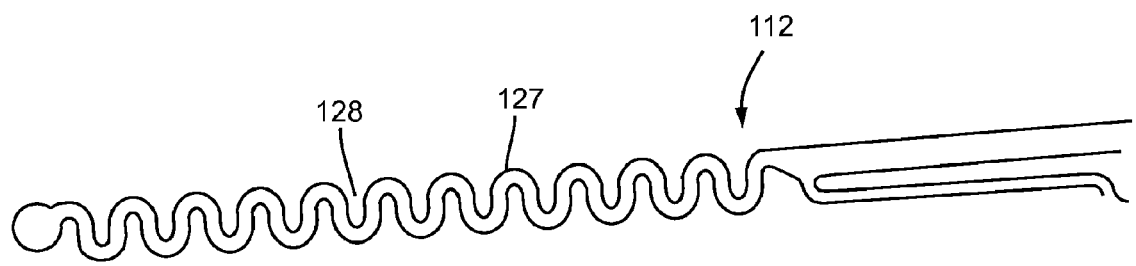

The distal tips 112 on the open end 144b of the cage 144 may provide a substantially atraumatic distal end for the cage 144, e.g., to prevent puncture or other damage to a wall of a body lumen within which the cage 144 is deployed. In addition or alternatively, the distal tips 112 may be sufficiently flexible to allow the distal tips 112 to twist helically and/or interlock with one another during use. FIGS. 15A-15C show alternative configurations of a distal tip that may be provided on the cage 144, e.g., to facilitate engaging and/or removing obstructive material within a body lumen. For example, FIG. 15A shows an exemplary embodiment of a distal tip 112a that includes a substantially straight configuration with a smooth leading edge 125.

Alternatively, FIG. 15B shows another exemplary embodiment of a distal tip 112b that includes a series of slots or indentations 126 spaced apart along a length of the distal tip 112b, e.g., that may allow the distal tips 112b to entangle with each other and/or with the obstructive material captured or otherwise engaged by the distal tips 112b to facilitate removal, as described further below with reference to FIGS. 16A-16H. For example, when the cage 144 is rotated, the distal tips 112b and obstructive material may be wound together, e.g., such that portions of other distal tips 112b and/or obstructive material may enter the slots 126 and the distal tips 112b become interlocked with one another. FIG. 15C shows yet another exemplary embodiment of a distal tip 112c that includes a serpentine pattern 127. In this embodiment, the internal bends 128 of the serpentine pattern 127 may provide regions where other distal tips 112c and/or obstructive material may become entangled, e.g., compared to providing a smooth edge 125, as shown in the distal tip 112a of FIG. 15A.

One advantage of the cage 144 shown in FIGS. 11A-13 is that the cage 144 may facilitate deploying the cage 144 and/or advancing the cage 144 into or through obstructive material within a body lumen. In contrast, the cage 44 shown in FIG. 1 is generally maintained substantially stationary upon deployment within a body lumen, e.g., while the obstruction device 40 is retracted to withdraw obstructive material into the cage 44. For example, the cage 144 of FIGS. 11A-13 may facilitate pulling material 52 back into the open end 144a of the cage 144 and/or separating obstructive material from a wall of the body lumen 50.

During distal advancement, the cage 144 may be concurrently advanced and rotated, e.g., manually or using a driveshaft connected to an electric motor in a handle (not shown) of the apparatus 10 (see, e.g., FIG. 1). This may cause the distal tips 112 of the cage 144 to track along the inside wall of the body lumen 50, e.g., in a helical manner as the cage 144 is advanced. When thrombus or other obstructive material is encountered, the distal tips 112 may pass between the material 52 and the wall of the body lumen 50, thereby positioning the material 50 inside the cage 144.

The distal tips 112 of the cage 144 may facilitate separation and/or capture of material within the cage 144. For example, the edges of the distal tips 112 may provide distal leading edges of the cage 144 that are not a substantially smooth cylinder but define an undulating surface. Consequently, the distal tips 112 of the cage 144 may act as a saw by repeatedly making contact with the material 52 as the cage 144 is rotated, which may increase the chance of material 52 being dislodged from the wall of the body lumen 50 and/or captured within the cage 144. To further ensure that the leading edge of the cage 144 passes between the unwanted material and the wall of the body lumen 50, the distal tips 112 and/or edges of the struts 116, 118 may also act as blades shearing along the wall of the body lumen 50 to draw adherent material into the cage 144. Thus, the struts 116, 118 may cut or otherwise separate the interface between the body lumen 50 and the obstructive material 52.

The distal tips 112 may be formed such that they conform substantially to the cylindrical shape of the cage 144, e.g., defining a diameter similar to the rest of the expanded cage 144, although alternatively the distal tips 112 may be biased radially outwardly, e.g., to ensure that the distal tips 112 pass between the wall of the body lumen 50 and the obstructive material 52 and/or enhance engagement of the distal tips 112 against the wall of the body lumen 50. Alternatively, the distal tips 112 may by biased to extend radially inwardly, e.g., laterally inwardly, relative to a central longitudinal axis of the apparatus 10, e.g., to prevent substantial risk of damage to the wall of the body lumen 50.

Figure 13:
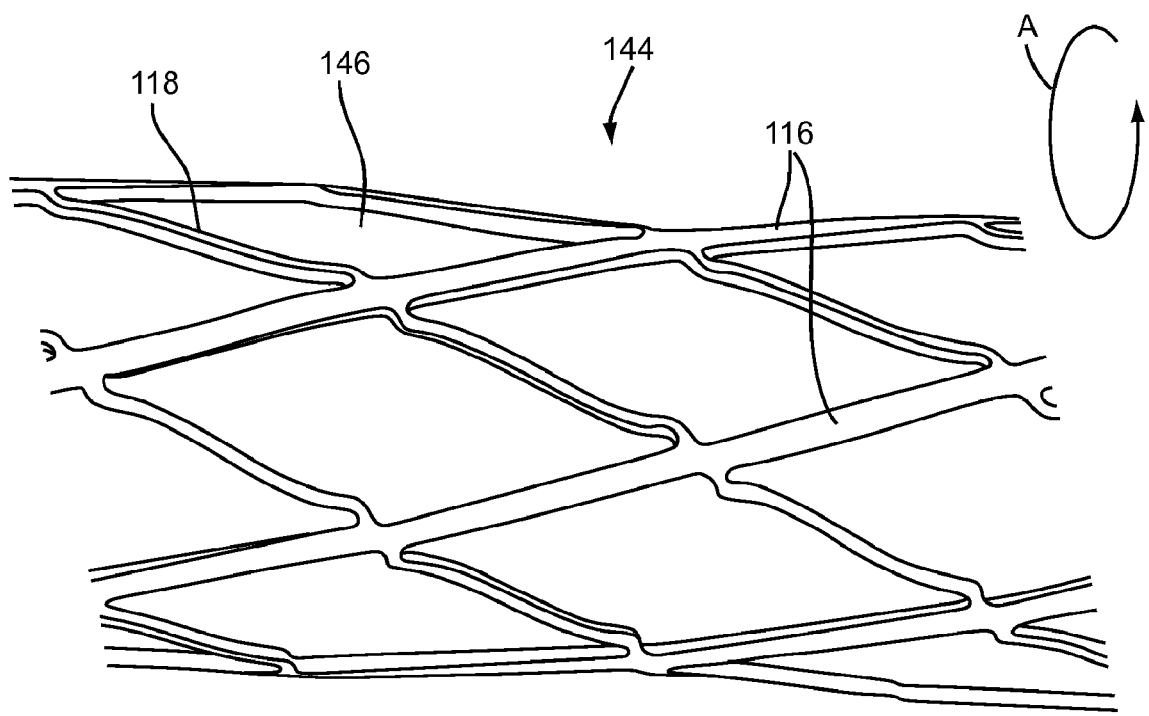
FIG. 13 is a perspective detail of the macerator device cage shown in FIGS. 11A and 11B being rotated in a direction A.

In addition, the different thicknesses and/or shapes of struts 116, 118 may provide a cage 144 that responds in different ways depending upon which direction the cage 40 is rotated. For example, arrow "A" in FIG. 13 represents a first direction for rotation of the cage 144. If resistance is encountered in the portions of the cage 144 contacting the wall of the body lumen 50 (not shown) during this rotation, torsion may occur. Because the thick struts 116 have a relatively high resistance to bending and the thin struts 118 are easily bent, the torsion may not bend the thick struts 116, but may cause the thin struts 118 to bend to define a greater angle between the adjacent struts 116, 118 and expand the cage 144 radially outwardly. This may increase the contact force between the macerator cage 144, e.g., leading edges of the thick struts 116, and the wall of the body lumen 50, which may increase the chance that obstructive material being removed from the wall of the body lumen 50 and being captured within the cage 144.

Optionally, the leading edges of the thick struts 116 may include sharpened edges or other features, which may enhance cutting or other engagement with adherent material within the body lumen 50.

If the cage 144 is rotated in a second direction opposite to "A," the torsion may cause the thin struts 118 to bend due to their low column strength to reduce the angle between the adjacent struts 116, 118, and the cage 144 may not expand radially outwardly in the same manner as the first direction.

This anisotropy with respect to rotational direction may be useful because the cage 144 may be advanced and rotated in the "A" direction to engage and separate adherent obstructive material from a vessel wall, e.g., causing the material to enter into the cage 144. The torsion may also cause the cage 144 to expand outwardly for better apposition or engagement with the vessel wall. If the cage 144 encounters excessive resistance, the cage 144 may be rotated in the second direction, e.g., to disengage the resistance without causing radial expansion.

Depending on the stiffness differential between the thin and thick struts 118, 116, rotation of the cage 144 in the second direction may also cause the cage 144 to radially contract to further facilitate disengagement.

Figure 14A:
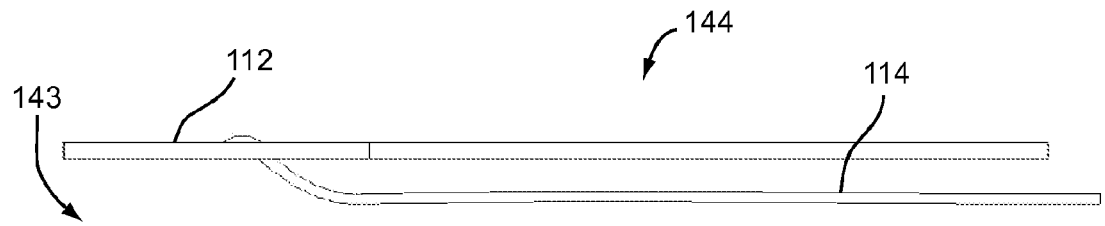
FIGS. 14A and 14B are cross-sectional views of another exemplary embodiment of a macerator device cage that includes control wires for directing a distal end of the cage between an open configuration and a closed configuration, respectively.
Figure 14B:
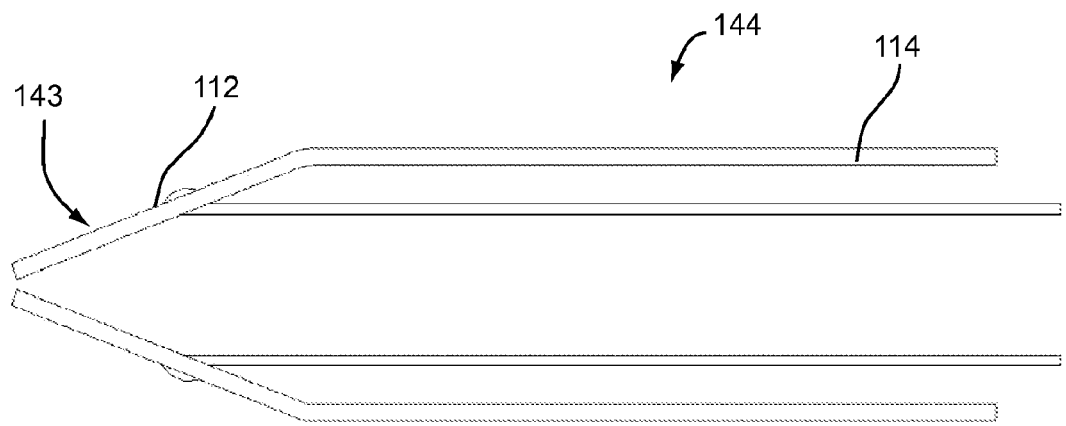
Figure 14C:
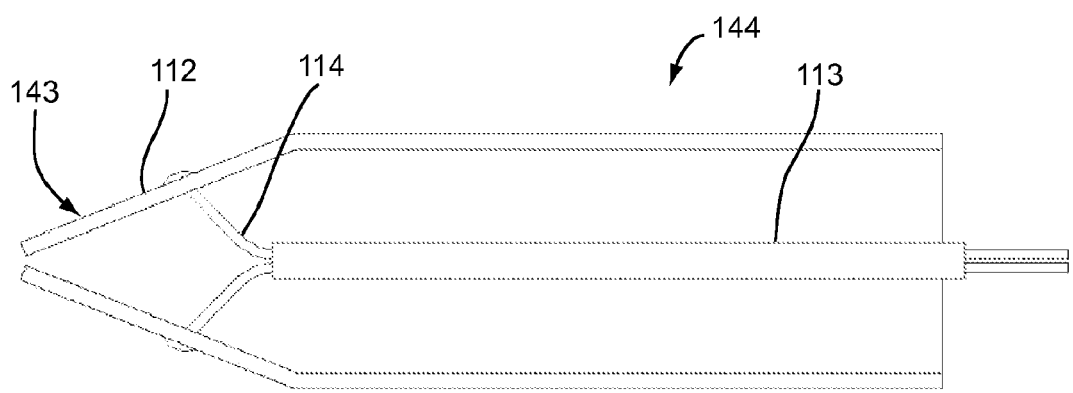
FIG. 14C is a cross-sectional view of an alternative embodiment of the macerator device cage of FIGS. 14A and 14B that includes control wires and a sleeve around the control wires for directing the cage between an open configuration and a closed configuration.

Turning to FIGS. 14A-14C, yet another embodiment of an expandable cage 144 is shown, which may include an actuation mechanism for selectively opening and/or closing an open distal end 143 of the cage 144. For example, the distal end 143 of the cage 144 may be substantially closed by contracting the distal tips 112 radially inwardly, e.g., using control elements, e.g., one or more wires or filaments 114, coupled to each of the distal tips 112. Alternatively, a single control element (not shown) may be threaded through each of the distal tips 112, e.g., circumferentially and successively through holes in the distal tips (not shown), such that proximal tension on the control element may bend or otherwise direct the distal tips 122 radially inwardly. Optionally, a locking mechanism (not shown) may be provided for securing the distal tips 122 in the closed orientation, if desired. Alternatively, the distal tips 122 may interlock with one another, e.g., as described above, to secure the distal tips 122 in the closed orientation.

FIG. 14A shows the distal end 143 open with the cage 144 in the expanded configuration, e.g., with the control elements 114 relaxed and the distal tips 112 biased to a substantially axial, open configuration. FIG. 14B shows the distal tips 112 bent or otherwise directed inwardly towards a closed configuration, e.g., after proximal tension is applied to the control elements 114. The structure of the distal tips 112 may facilitate this bending by providing one or more preferential bending features, e.g., thinned strut widths, thinned strut thicknesses, perforated portions, and the like (not shown), to provide hinged regions of the distal tips 112. In an alternative embodiment, shown in FIG. 14C, a tubular member 113 may be advanced over the control elements 114 to cause the distal tips 112 to bend radially inwardly.

The closed configurations shown in FIGS. 14B and 14C may allow obstructive material captured within the cage 114 to be substantially retained therein, e.g., without the need for an expandable obstruction member 34, as described elsewhere herein. In these alternatives, the cage 144 may simply be withdrawn into a constraint tube or access sheath (not shown), thereby compressing the cage 144 radially inwardly.

With the distal tips 112 closed, the captured material may not simply escape out the distal end 143 of the cage 144, but may remain within the cage 144 to be extruded through the apertures 146 (not shown in FIGS. 14B and 14C) as the cage is compressed, e.g., to be aspirated, as described above.

Alternatively, the captured material may be withdrawn into the constraint tube or sheath along with the cage 144, also as described above.

Figure 16A:
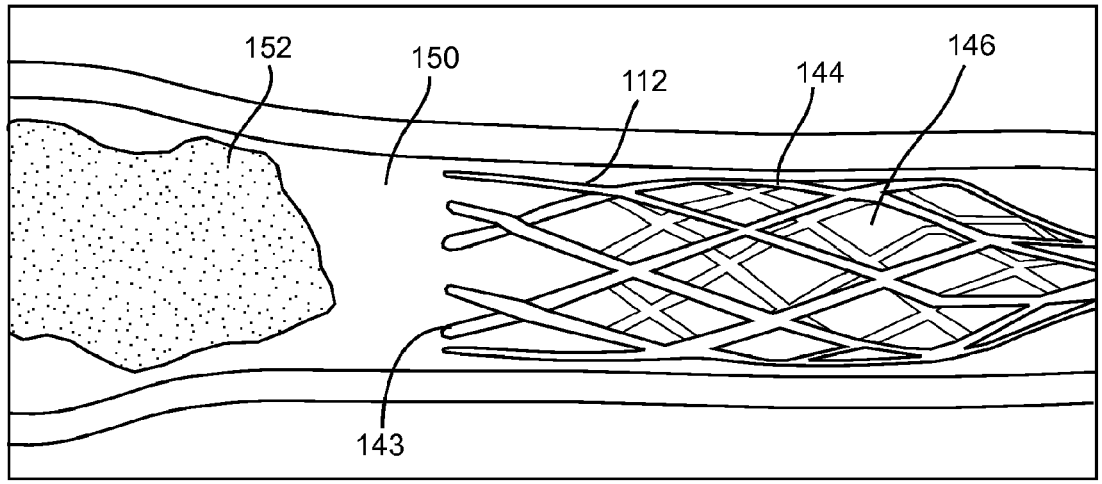
FIGS. 16A-16H are cross-sectional views of a body lumen within a patient's body, showing another method for removing obstructive material within the body lumen.

Turning to FIGS. 16A-16H, another exemplary method is shown for removing obstructive material from within a vessel or other body lumen 150, e.g., using the cage 144 shown in FIGS. 11A-13. The cage 144 may be introduced into the body lumen 150 via an access sheath and/or constraint tube 148, similar to the previous embodiments. As shown in FIG. 16A, the cage 144 has been deployed and expanded within the body lumen 150 such that the open distal end 143 is disposed adjacent to obstructive material 152 intended to be removed. Once fully expanded, the cage 144 may be rotated and advanced within the body lumen 150 toward the obstructive material 152.

Figure 16B:
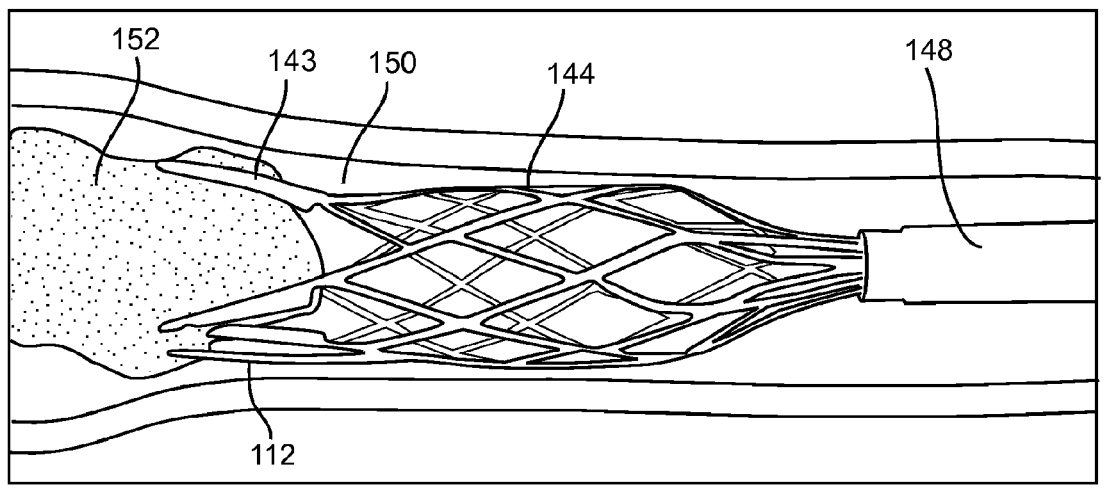

Turning to FIG. 16B, the distal end 143 of the cage 144 may engage the material 152, e.g., such that the distal tips 112 pass between the material 152 and the wall of the body lumen 152 to some degree, but are also free to deform as they become entangled in the material 152. Optionally, an obstruction device (not shown) may be introduced through the material 152 and an obstruction member expanded beyond the material 152 before the cage 144 is advanced. Thus, the obstruction member may prevent distal migration of the material 152 away from the cage 144 as the cage 144 is advanced.

Figure 16C:
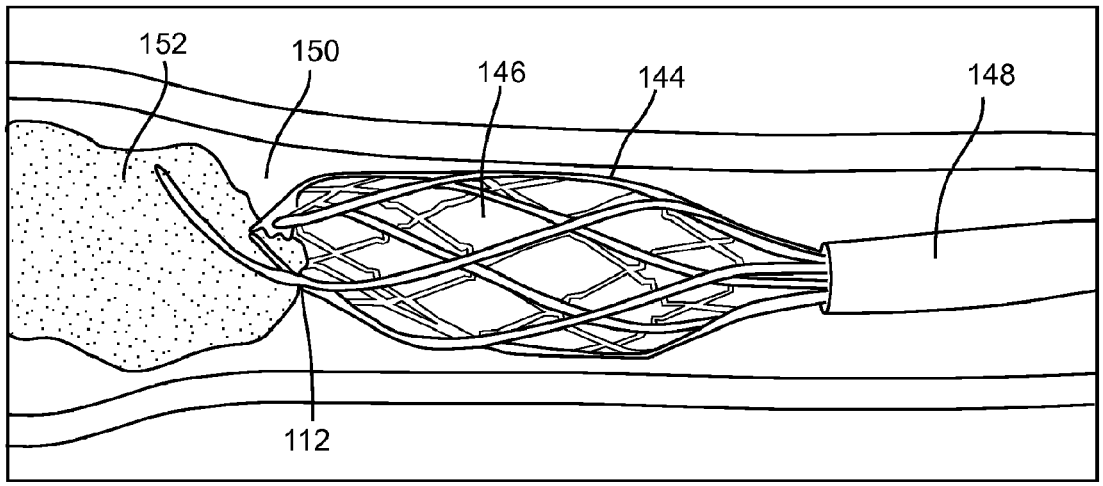
Figure 16D:
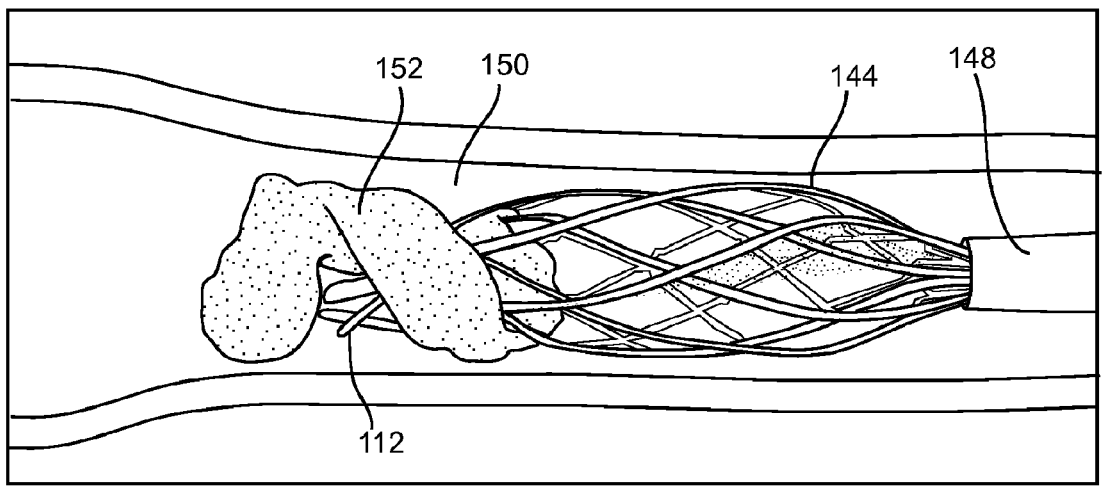

With additional reference to FIG. 16C, upon further rotation of the cage 144, the distal tips 112 may wind at least partially around the material 152 and/or around each other, thereby creating a mechanical engagement between the cage 144 and the material 152. Further rotation of the cage 144 may then be transmitted to the material 152, which may cause the material 152 to twist and/or otherwise detach from the wall of the body lumen 150. After entanglement and further rotation, the entangled material 152 may be completely removed from the wall of the body lumen 150, as shown in FIG. 16D.

Figure 16E:
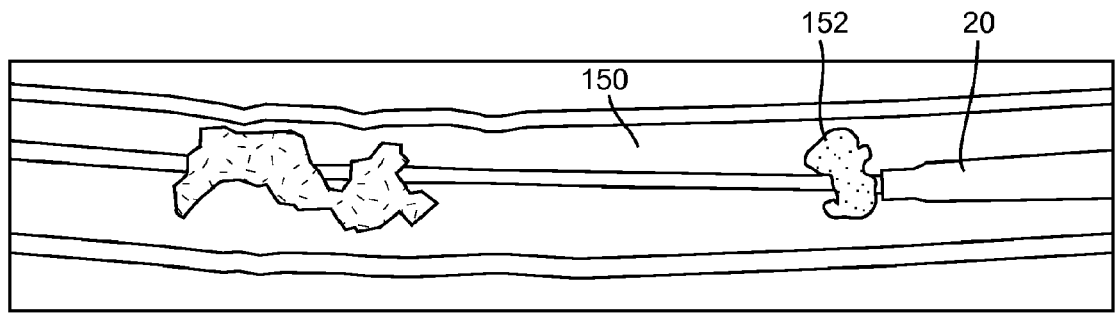

As shown in FIG. 16E, the cage 144 may then be withdrawn into the access sheath and/or constraint tube 148, similar to the previous embodiments, thereby compressing the cage 144 radially inwardly towards the collapsed configuration. Because the distal tips 112 of the cage 144 are substantially straight and free on their distal ends (i.e. the cage 144 is open ended and not attached to a core wire on its distal end), the distal tips 112 may be disengaged and the material 152 released as the cage 144 is withdrawn into the access sheath 20. Thus, the separated material 152 may remain loose within the body lumen 150, as shown.

Figure 16F:
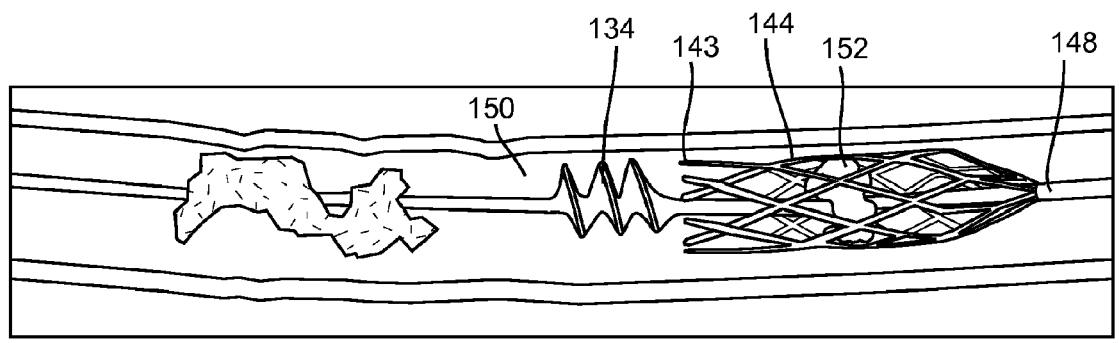

Thereafter, as shown in FIG. 16F, the cage 144 may be redeployed from the constraint tube 148 or sheath and expanded again with the open end 143 disposed adjacent the loose material 152. The material 152 may then be pulled into the open end 143 of the cage 144, e.g., using an obstruction device 134, which may be the same device deployed beyond the material 152 previously or a different device introduced into the body lumen 150 and beyond the material 152 before or after redeploying the cage 144.

Figure 16G:
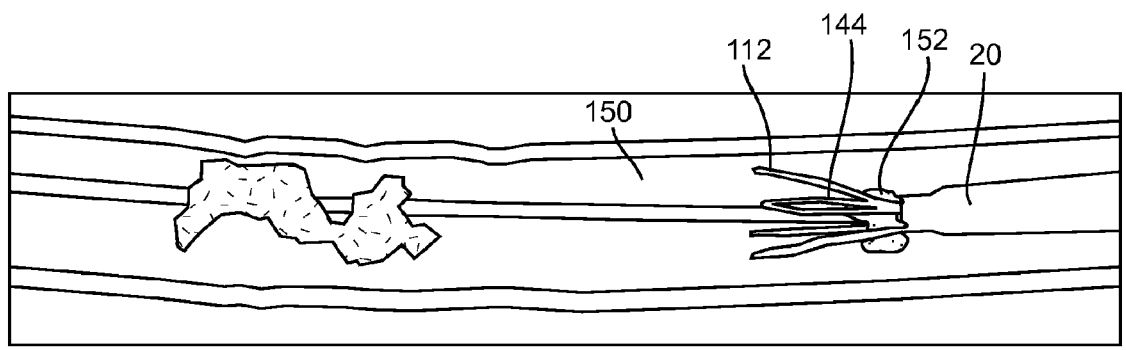
Figure 16H:
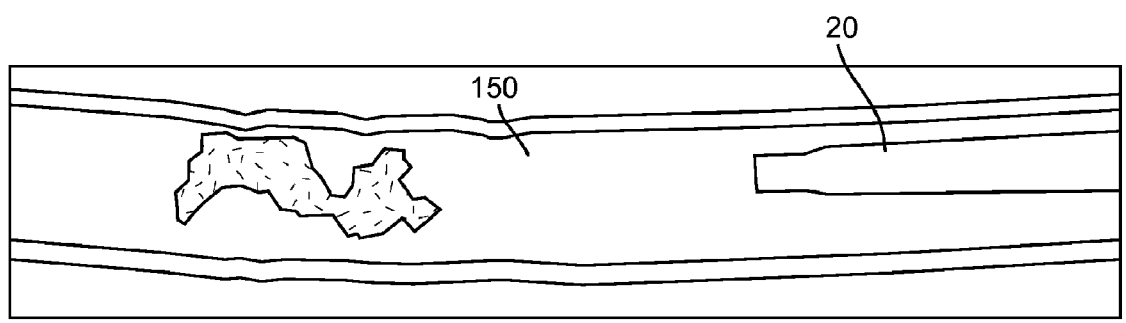

Turning to FIG. 16G, the cage 144 with the material 152 captured therein may then be withdrawn into the sheath 20 or constraint tube (not shown), similar to the previous embodiments. As discussed elsewhere herein, any material that protrudes through the apertures 146 in the cage 144 may be sheared off or otherwise separated as the cage 144 is compressed, e.g., to ensure that the cage 144 does not become lodged in the tip of the sheath 20. The cage 144 may be withdrawn completely into the sheath 20, as shown in FIG. 16H, and any remaining loose particles of the material 152 may be aspirated through the sheath lumen, similar to the previous embodiments. For example, as described above, a vacuum may be applied by the sheath 20 within the body lumen 150 at any time to aspirate loose particles within the body lumen 150, e.g., released when the cage 144 is used to separate material from the wall of the body lumen 150 or thereafter. Any of these steps may be repeated as many times as desired to remove any remaining material.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

The invention claimed is:

1. A system for removing obstructive material from a body lumen, the system comprising:
   an outer tubular member comprising a proximal end, a distal end sized for introduction into a body lumen, and a lumen extending between the proximal and distal ends;
   an obstruction device deployable from the outer tubular member to a location distal of an entirety of the obstructive material intended to be removed, the obstruction device comprising a first shaft configured to slide within the outer tubular member and a balloon on a distal end of the first shaft; and
   a macerator device comprising:
      an expandable cage carried on a distal end of a second shaft configured to slide within the outer tubular member, the second shaft being different from the first shaft;
      a constraint tube for maintaining the cage in a collapsed configuration to allow the macerator device to be introduced into the body lumen through the lumen of the outer tubular member, the cage being deployable from a distal end of the constraint tube and expandable to an expanded configuration within the body lumen at a location at least partially proximal of the obstructive material intended to be removed, the cage comprising a closed end connected to the distal end of the second shaft and an open end, that is opposite the closed end, communicating with an interior of the cage in the expanded configuration for capturing obstructive material within the interior of the cage; and
      a plurality of separate substantially straight distal tips extending distally of the open end of the cage, each substantially straight distal tip comprising a proximal end and a distal end, the proximal ends of the substantially straight distal tips being connected to the open end of the cage, the substantially straight distal tips being configured to interlock with one another when the cage is rotated, and the distal ends of the substantially straight distal tips being atraumatic,
   wherein the cage is retractable into the constraint tube after being expanded within a body lumen such that the closed end of the cage slidably engages the distal end of the constraint tube and the cage is compressed to the collapsed configuration.

2. The system of claim 1, wherein the cage comprises a tubular structure including a wall extending between the open end and the closed end of the cage, the wall comprising a plurality of apertures defining a pore size such that, when the cage slidably engages the distal end of the constraint tube as the cage is retracted into the constraint tube, obstructive material captured by the cage that extends through the apertures is separated from the cage by the distal end of the constraint tube.

3. The system of claim 2, further comprising a source of vacuum coupled to the lumen of the outer tubular member for aspirating obstructive material separated from the cage into the lumen of the outer tubular member.

4. The system of claim 1, wherein the second shaft of the macerator device comprises a lumen extending between proximal and distal ends thereof for slidably receiving the obstruction device therein with the balloon in a collapsed configuration.

5. The system of claim 1, wherein the cage comprises a tubular structure including a wall extending between the open end and the closed end of the cage.

6. The system of claim 5, wherein the wall of the cage comprises a plurality of struts defining a plurality of apertures.

7. The system of claim 6, wherein the substantially straight distal tips extend from the plurality of struts of the open end of the cage.

8. The system of claim 6, wherein the cage comprises a plurality of features extending inwardly from the wall for engaging obstructive material captured within the interior of the cage.

9. The system of claim 8, further comprising an access sheath comprising a proximal end, a distal end sized for introduction into a body lumen, and a lumen extending between the proximal and distal ends, the outer tubular member sized to be slidably received within the lumen of the access sheath.

10. The system of claim 9, further comprising an embolectomy device deployable from the access sheath, the embolectomy device comprising an expandable member for directing obstructive material into the open end of the cage when the cage is in the expanded configuration within a body lumen.

11. The system of claim 1, further comprising one or more control elements coupled to the substantially straight distal tips, the control elements actuatable for drawing the substantially straight distal tips inwardly towards a closed configuration with the cage in the expanded configuration to prevent obstructive material captured within the cage from escaping out the open end.

12. The system of claim 11, wherein the cage is biased to expand to the expanded configuration and is resiliently compressible inwardly towards the collapsed configuration.

13. The system of claim 1, wherein the second shaft of the macerator device is configured to slide within the outer tubular member and over the first shaft of the obstruction device.

14. The system of claim 1, wherein the distal end of the constraint tube is a sharp edge.

15. The system of claim 1, wherein the atraumatic distal ends of the substantially straight distal tips are rounded.

16. The system of claim 1, wherein the substantially straight distal tips comprise one or more bending features.

17. A system for removing obstructive material from a body lumen, the system comprising:

an outer tubular member comprising a proximal end, a distal end sized for introduction into a body lumen, and a lumen extending between the proximal and distal ends; and a macerator device deployable from the lumen and comprising an elongate shaft, an expandable cage carried on a distal end of the elongate shaft, and a constraint tube having a distal opening with a sharp edge, wherein the cage comprises a closed end connected to the distal end of the elongate shaft and an open end, that is opposite the closed end, communicating with an interior of the cage in an expanded configuration for capturing obstructive material within the interior of the cage, wherein the cage comprises a wall extending between the open end and the closed end of the cage, the wall comprising a plurality of struts defining a plurality of apertures, wherein the elongate shaft and the cage are axially moveable relative to the constraint tube such that the closed end of the cage slidably engages the sharp distal edge of the constraint tube to compress the cage to a collapsed configuration so that obstructive material captured by the cage extends through the apertures of the wall of the cage, wherein the sharp edge of the constraint tube is configured to shear the obstructive material extending through the apertures from the cage, and wherein a plurality of separate substantially straight distal tips extend distally from the struts of the open end of the cage, each of the substantially straight distal tips comprising a proximal end and a distal end, the proximal ends of the substantially straight distal tips being connected to the open end of the cage, the substantially straight distal tips being configured to interlock with one another when the cage is rotated, and the distal ends of the substantially straight distal tips being atraumatic.

18. The system of claim 17, further comprising an elongate treatment member comprising a balloon selectively expandable for directing the obstructive material within the body lumen into the cage when the cage is in the expanded configuration.

19. The system of claim 18, wherein the elongate treatment member is insertable through a lumen in the elongate shaft of the macerator device.

20. The system of claim 19, wherein the elongate treatment member is insertable through the lumen of the outer tubular member adjacent to the elongate shaft of the macerator device.

21. The system of claim 20, wherein the cage comprises an uninterrupted path through which the elongate treatment member passes.

22. The system of claim 17, wherein an inner surface of the cage comprises a plurality of features extending inwardly for engaging obstructive material captured within the cage.

23. The system of claim 17, wherein the constraint tube is fixedly coupled to an inner surface of the outer tubular member.

24. The system of claim 17, further comprising an obstruction device deployable from the outer tubular member to a location distal of an entirety of the obstructive material intended to be removed.

25. The system of claim 24, wherein the obstruction device comprises a first shaft configured to slide within the outer tubular member and an expandable member on a distal end of the first shaft.

26. The system of claim 17, wherein the atraumatic distal ends of the substantially straight distal tips are rounded.

27. The system of claim 17, wherein the substantially straight distal tips comprise one or more bending features.

* * * * *